(12) United States Patent
Ashikaga et al.

(10) Patent No.: US 10,271,905 B2
(45) Date of Patent: Apr. 30, 2019

(54) PATIENT-SPECIFIC VIRTUAL INTERVENTION LABORATORY TO PREVENT STROKE

(71) Applicant: THE JOHNS HOPKINS UNIVERSITY, Baltimore, MD (US)

(72) Inventors: Hiroshi Ashikaga, Lutherville, MD (US); Tomohiro Otani, Osaka (JP)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 15/567,725

(22) PCT Filed: Apr. 20, 2016

(86) PCT No.: PCT/US2016/028435
§ 371 (c)(1),
(2) Date: Oct. 19, 2017

(87) PCT Pub. No.: WO2016/172206
PCT Pub. Date: Oct. 27, 2016

(65) Prior Publication Data
US 2018/0116725 A1 May 3, 2018

Related U.S. Application Data

(60) Provisional application No. 62/150,157, filed on Apr. 20, 2015, provisional application No. 62/258,353, filed on Nov. 20, 2015.

(51) Int. Cl.
*A61B 5/00* (2006.01)
*A61B 5/055* (2006.01)
(Continued)

(52) U.S. Cl.
CPC ............ *A61B 34/10* (2016.02); *A61B 5/0044* (2013.01); *A61B 5/055* (2013.01); *A61B 5/4064* (2013.01);
(Continued)

(58) Field of Classification Search
CPC ..... A61B 34/10; A61B 5/0044; A61B 5/0055; A61B 5/4064; A61B 5/7275; A61B 6/032;
(Continued)

(56) References Cited

U.S. PATENT DOCUMENTS 9,629,615 B1 * 4/2017 Tavakoli .............. A61B 8/5223
10,068,669 B2 * 9/2018 Mansi .................... G16H 50/50
(Continued)

FOREIGN PATENT DOCUMENTS

WO 2014127320 A1 8/2014

OTHER PUBLICATIONS

Mozaffarian, et al., Heart disease and stroke statistics—2015 update: a report from the American Heart Association. Circulation 2015; 131: e-29-322.
(Continued)

*Primary Examiner* — Ali Bayat
(74) *Attorney, Agent, or Firm* — Johns Hopkins Technology Ventures

(57) ABSTRACT

The present application relates to systems and methods for performing a computerized cardiac simulation for at least one of diagnosis, risk assessment or treatment planning including: receiving, by a computer, a plurality of three-dimensional cardiac images of a subject's heart such that each three-dimensional cardiac image corresponds to a different phase of a single cardiac cycle of the subject's heart; modeling structure, using the computer, of the left atrium of the subject as a function of time using the plurality
(Continued)

of three-dimensional cardiac images of the subject's heart; modeling blood flow, using the computer, within, into and out of the left atrium of the subject as a function of time using computational fluidic dynamics and using structure of said left atrium obtained from at least one of said plurality of three-dimensional cardiac images or said modeling structure of said left atrium; simulating at least one of time dependent structural function or time-dependent blood flow of said left atrium using results from said modeling structure and said modeling blood flow for a selected period of time; and providing information to a user from said simulating for use in at least one of diagnosis, risk assessment or treatment planning for a physiological effect related to function of said left atrium of the subject.

20 Claims, 15 Drawing Sheets

(51) Int. Cl.
| | | |
|---|---|---|
| A61B 34/10 | (2016.01) | |
| G06T 17/00 | (2006.01) | |
| G09B 23/28 | (2006.01) | |
| A61B 6/00 | (2006.01) | |
| G16H 50/50 | (2018.01) | |
| A61B 6/03 | (2006.01) | |
| A61B 8/08 | (2006.01) | |
| G06T 7/00 | (2017.01) | |
| G06T 17/20 | (2006.01) | |
| G06F 19/00 | (2018.01) | |
| G16H 50/30 | (2018.01) | |
| G16H 30/40 | (2018.01) | |

(52) U.S. Cl.
CPC ............ *A61B 5/7275* (2013.01); *A61B 6/032* (2013.01); *A61B 6/037* (2013.01); *A61B 6/503* (2013.01); *A61B 6/5211* (2013.01); *A61B 6/5217* (2013.01); *A61B 8/0883* (2013.01); *A61B 8/5223* (2013.01); *G06F 19/00* (2013.01); *G06T 7/0016* (2013.01); *G06T 17/00* (2013.01); *G06T 17/20* (2013.01); *G09B 23/288* (2013.01); *G16H 50/50* (2018.01); *A61B 2034/105* (2016.02); *G06T 2200/04* (2013.01); *G06T 2200/08* (2013.01); *G06T 2207/10081* (2013.01); *G06T 2207/10088* (2013.01); *G06T 2207/10104* (2013.01); *G06T 2207/10108* (2013.01); *G06T 2207/10132* (2013.01); *G06T 2207/30048* (2013.01); *G06T 2207/30104* (2013.01); *G06T 2210/41* (2013.01); *G16H 30/40* (2018.01); *G16H 50/30* (2018.01)

(58) Field of Classification Search
CPC ....... A61B 6/037; A61B 6/503; A61B 6/5211; A61B 6/5217; A61B 8/0883; A61B 8/5223; G06F 19/00; G06F 19/321; G06T 7/0016; G06T 17/00; G06T 17/20; G09B 23/288; G16H 50/50; G16H 50/30; G16H 10/60; G16H 30/40
USPC ........................................................ 382/131
See application file for complete search history.

(56) References Cited

U.S. PATENT DOCUMENTS

| | | | | |
|---|---|---|---|---|
| 2014/0071125 A1* | 3/2014 | Burlina | .................... | G06T 17/00 345/420 |
| 2015/0045662 A1 | 2/2015 | Kim et al. | | |
| 2015/0297161 A1* | 10/2015 | Grass | ..................... | A61B 6/503 600/426 |
| 2016/0034665 A1* | 2/2016 | Adirovich | ............ | A61B 5/0044 703/9 |
| 2016/0038246 A1* | 2/2016 | Wang | ........................ | G06T 7/73 600/429 |

OTHER PUBLICATIONS

Hart, Atrial fibrillation and stroke prevention. N Engl J Med. 2003;349:1015-1016.

Benjamin, et al., Left atrial size and the risk of stroke and death. The Framingham Heart Study. Circulation. 1995;92:835-841.

Wong, et al., Relation of left atrial dysfunction to ischemic stroke in patients with coronary heart disease (from the heart and soul study). Am J Cardiol. 2014;113:1679-1684.

Russo, et al., LA volumes and reservoir function are associated with subclinical cerebrovascular disease: the CABL (Cardiovascular Abnormalities and Brain Lesions) study. JACC Cardiovasc Imaging. 2013;6:313-323.

Habibi, et al., Association of left atrial function and left atrial enhancement in patients with atrial fibrillation: cardiac magnetic resonance study. Circ Cardiovasc Imaging. 2015;8:e002769.

Shih, et al., Association of decreased left atrial strain and strain rate with stroke in chronic atrial fibrillation. J Am Soc Echocardiogr. 2011;24:513-519.

Obokata, et al., Left atrial strain provides incremental value for embolism risk stratification over CHA(2)DS(2)-VASc score and indicates prognostic impact in patients with atrial fibrillation. J Am Soc Echocardiogr. 2014;27:709-716 e704.

January, et al., 2014 AHA/ACC/HRS Guideline for the Management of Patients With Atrial Fibrillation: A Report of the American College of Cardiology/American Heart Association Task Force on Practice Guidelines and the Heart Rhythm Society. Circulation. 2014,130:e199-267.

Habibi, et al., Association of CMR-measured LA function with heart failure development: results from the MESA study. JACC Cardiovasc Imaging. 2014;7:570-579.

Imai, et al., Multi-ethnic study of atherosclerosis: association between left atrial function using tissue tracking from cine MR imaging and myocardial fibrosis. Radiology. 2014;273:703-713.

Inaba, et al., Strain rate imaging for noninvasive functional quantification of the left atrium: comparative studies in controls and patients with atrial fibrillation. J Am Soc Echocardiogr. 2005;18:729-736.

Gage, et al., Validation of clinical classification schemes for predicting stroke. JAMA. 2001;285:2864-2870.

Lip, et al. Refining clinical risk stratification for predicting stroke and thromboembolism in atrial fibrillation using a novel risk factor-based approach. Chest. 2010;137:263-272.

Rivard, et al., Improved outcome following restoration of sinus rhythm prior to catheter ablation of persistent atrial fibrillation: a comparative multicenter study. Heart Rhythm. 2012;9:1025-1030.

Khurram, et al., Magnetic resonance image intensity ratio, a normalized measure to enable interpatient comparability of left atrial fibrosis. Heart Rhythm. 2014;11:85-92.

Ujino, et al., Two-dimensional echocardiographic methods for assessment of left atrial volume. Am J Cardiol. 2006;98:1185-1188.

Nacif, et al., Left atrial volume quantification using cardiac MRI in atrial fibrillation: comparison of the Simpson's method with biplane area-length, ellipse, and three-dimensional methods. Diagn Interv Radiol. 2013;19:213-220.

Farzaneh-Far, et al., Left atrial passive emptying function during dobutamine stress MR imaging is a predictor of cardiac events in patients with suspected myocardial ischemia. JACC Cardiovasc Imaging. 2011;4:378-388.

Karabay, et al., Left atrial deformation parameters predict left atrial appendage function and thrombus in patients in sinus rhythm with suspected cardioembolic stroke. Echocardiography. 2013;30:572-581.

(56) References Cited

OTHER PUBLICATIONS

Stoddard, et al., Left atrial appendage thrombus is not uncommon in patients with acute atrial fibrillation and a recent embolic event: a transesophageal echocardiographic study. J Am Coll Cardiol. 1995;25:452-459.

Khan, Transient atrial mechanical dysfunction (stunning) after cardioversion of atrial fibrillation and flutter. Am Heart J. 2002;144:11-22.

Daccarett, et al., Association of left atrial fibrosis detected by delayed-enhancement magnetic resonance imaging and the risk of stroke in patients with atrial fibrillation. J Am Coll Cardiol. 2011;57:831-838.

Maceira, et al., Reference left atrial dimensions and volumes by steady state free precession cardiovascular magnetic resonance. J Cardiovasc Magn Reson. 2010;12:65.

Hof, et al., Left atrial volume and function assessment by magnetic resonance imaging. J Cardiovasc Electrophysiol. 2010;21:1247-1250.

Motoki, et al., Assessment of left atrial mechanics in patients with atrial fibrillation: comparison between two-dimensional speckle-based strain and velocity vector imaging. J Am Soc Echocardiogr. 2012;25:428-435.

Schmidt, et al., Navigated DENSE strain imaging for post-radiofrequency ablation lesion assessment in the swine left atria. Europace. 2014;16:133-141.

Rathi, et al., Contrast-enhanced CMR is equally effective as TEE in the evaluation of left atrial appendage thrombus in patients with atrial fibrillation undergoing pulmonary vein isolation procedure. Heart Rhythm. 2013;10:1021-1027.

Osranek, et al., Left atrial volume predicts cardiovascular events in patients originally diagnosed with lone atrial fibrillation: three-decade follow-up. Eur Heart J. 2005;26:2556-2561.

Tsang, et al., Effects of quinapril on left atrial structural remodeling and arterial stiffness. Am J Cardiol. 2006;97:916-920.

Perea, et al., Left atrial contractility is preserved after successful circumferential pulmonary vein ablation in patients with atrial fibrillation. J Cardiovasc Electrophysiol. 2008;19:374-379.

Wolf, et al., Original Contributions Atrial Fibrillation as an Independent Risk Factor for Stroke☐: The Framingham Study. Stroke. 1991:983-988.

Brambatti, et al., Temporal relationship between subclinical atrial fibrillation and embolic events. Circulation. 2014;129(21):2094-2099.

Daoud, et al., Temporal relationship of atrial tachyarrhythmias, cerebrovascular events, and systemic emboli based on stored device data: A subgroup analysis of TRENDS. Hear Rhythm. 2011;8(9):1416-1423.

Inoue, et al., Quantitative Tissue-Tracking Cardiac Magnetic Resonance (CMR) of Left Atrial Deformation and the Risk of Stroke in Patients with Atrial Fibrillation. J Am Heart Assoc. 2015;4(4):e001844-e001844.

Al-Issa, et al., Regional function analysis of left atrial appendage using motion estimation CT and risk of stroke in patients with atrial fibrillation. Eur Hear J—Cardiovasc Imaging. 2015:jev207.

Zhang, et al., Characterizing left atrial appendage functions in sinus rhythm and atrial fibrillation using computational models. J Biomech. 2008;41(11):2515-23.

Koizumi, et al., Numerical analysis of hemodynamic changes in the left atrium due to atrial fibrillation. J Biomech. 2015;48(3):472-478.

Pourmorteza, et al., A new method for cardiac computed tomography regional function assessment: stretch quantifier for endocardial engraved zones (SQUEEZ). Circ Cardiovasc Imaging. 2012;5(2):243-50.

Chnafa, et al., Image-based large-eddy simulation in a realistic left heart. Comput Fluids. 2014;94:173-187.

Smiseth, et al., The pulmonary venous systolic flow pulse—its origin and relationship to left atrial pressure. J Am Coll Cardiol. 1999;34(3):802-809.

Fyrenius, et al., Three dimensional flow in the human left atrium. Heart. 2001;86(4):448-455.

Agmon, et al., Echocardiographic assessment of the left atrial appendage. J. Am. Coll. Cardiol. 34:1867-1877, 1999.

Di Biase, et al., Does the left atrial appendage morphology correlate with the risk of stroke in patients with atrial fibrillation? Results from a multicenter study. J. Am. Coll. Cardiol. 60:531-538, 2012.

Blackshear, et al., Appendage obliteration to reduce stroke in cardiac surgical patients with atrial fibrillation. Ann. Thorac. Surg. 61:755-759, 1996.

Fatema, et al., Increased left atrial volume index: potent biomarker for first-ever ischemic stroke. Mayo Clin. Proc. 83:1107-1115, 2008.

Goubergrits, et al., Numerical dye washout method as a tool for characterizing the heart valve flow: study of three standard mechanical heart valves. ASAIO J. 54:50-57, 2008.

Healey, et al., Subclinical Atrial Fibrillation and the Risk of Stroke. N. Engl. J. Med. 366:120-129, 2012.

Kim, et al., A simulated dye method for flow visualization with a computational model for blood flow. J. Biomech. 37:1125-1136, 2004.

Kimura, et al., Anatomical characteristics of the left atrial appendage in cardiogenic stroke with low CHADS2 scores. Hear. Rhythm 10:921-925, 2013.

Tay, W., et al., "Towards patient-specific cardiovascular modeling system using the immersed boundary technique" Biomedical Engineering Online, 2011, vol. 10, Article No. 52, Internal pp. 1-17.

McDowell, K., et al., "Methodology for patient-specific modeling of atrial fibrosis as a substrate for atrial fibrillation" Journal of Electrocardiology, 2012, vol. 45, pp. 640-645.

Collins, T., et al., "Modeling and simulation approaches for cardiovascular function and their role in safety assessment" CPT: Pharmacometrics & Systems Pharmacology, Epub. Mar. 11, 2015, vol. 4, Article No. e18, Internal pp. 1-14.

Kizer, et al., Left atrial diameter as an independent predictor of first clinical cardiovascular events in middle-aged and elderly adults: The Strong Heart Study (SHS). Am. Heart J. 151:412-418, 2006.

Ku, Blood Flow in Arteries. Annu. Rev. Fluid Mech. 29:399-434, 1997.

Miller, et al., Diagnostic performance of coronary angiography by 64-row CT. N. Engl. J. Med. 359:2324-2336, 2008.

Morales, et al., A Virtual Coiling Technique for Image-Based Aneurysm Models by Dynamic Path Planning. IEEE Trans. Med. Imaging 1-11, 2012.

Ozer, et al., Left atrial appendage function in patients with cardioembolic stroke in sinus rhythm and atrial fibrillation. J. Am. Soc. Echocardiogr. 13:661-665, 2000.

Piccini, et al., Atrial fibrillation and stroke: It's not necessarily all about the rhythm. Heart Rhythm 8:1424-1425, 2011.

Seo, et al., Effect of diastolic flow patterns on the function of the left ventricle. Phys. Fluids 25:, 2013.

Sweby, High Resolution Schemes Using Flux Limiters for Hyperbolic Conservation Laws. SIAM J. Numer. Anal. 21:995-1011, 1984.

Vedula, et al., Hemodynamics in the left atrium and its effect on ventricular flow patterns. J. Biomech. Eng. , 2015.

Kalantarian, et al., Association between atrial fibrillation and silent cerebral infarctions: A systematic review and meta-analysis. Ann Intern Med. 2014;161(9):650-658.

Ezekowitz, et al., Silent cerebral infarction in patients with nonrheumatic atrial fibrillation. The veterans affairs stroke prevention in nonrheumatic atrial fibrillation investigators. Circulation. 1995;92(8):2178-2182.

Feinberg, et al., Epidemiologic features of asymptomatic cerebral infarction in patients with nonvalvular atrial fibrillation. Arch Intern Med. 1990;150(11):2340-2344.

Kalantarian, et al., Cognitive impairment associated with atrial fibrillation: A meta-analysis. Ann Intern Med. 2013;158(5 Pt 1):338-346.

Thacker, et al., Atrial fibrillation and cognitive decline: A longitudinal cohort study. Neurology. 2013;81(2):119-125.

Ott, et al., Atrial fibrillation and dementia in a population-based study. The rotterdam study. Stroke. 1997;28(2):316-321.

Miyasaka, et al., Risk of dementia in stroke-free patients diagnosed with atrial fibrillation: Data from a community-based cohort. Eur Heart J. 2007;28(16)1962-1967.

(56) References Cited

OTHER PUBLICATIONS

Alzheimer's Association. 2015 alzheimer's disease facts and figures. Alzheimers Dement. 2015;11(3):e332.
Di Tullio, et al., Left atrial size and the risk of ischemic stroke in an ethnically mixed population. Stroke. 1999;30(10):2019-2024.
Karadag, et al., Relationship between left atrial volume index and cognitive decline in elderly patients with sinus rhythm. J Clin Neurosci. 2013;20(8):1074-1078.
Alosco, et al., Left atrial size is independently associated with cognitive function. Int J Neurosci. 2013;123(8):544-552.
Oh, et al., Effect of cardiac function on cognition and brain structural changes in dementia. J Clin Neurol. 2012;8(2):123-129.
Otani, et al., A Computational Framework for Personalized Blood Flow Analysis in the Human Left Atrium. Ann Biomed Eng 2016; 44: 3284-3294.
Alissa, et al., Regional dysfunction of left atrial appendage and its association with stroke in atrial fibrillation Circulation. 2014;130:A18516.
Khurram, et al., Relationship between left atrial appendage morphology and stroke in patients with atrial fibrillation. Heart Rhythm 10:1843-9, 2013.
Seo, et al., Effect of the mitral valve on diastolic flow patterns. Phys. Fluids 26:121901, 2014.
Stavrakis, et al., Transesophageal echocardiographic assessment of pulmonary veins and left atrium in patients undergoing atrial fibrillation ablation. Echocardiography 28:775-781, 2011.
Tsang, et al., Prediction of risk for first age-related cardiovascular events in an elderly population: The incremental value of echocardiography. J. Am. Coll. Cardiol. 42:1199-1205, 2003.

\* cited by examiner

101

103          105

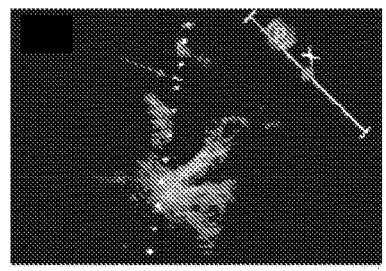 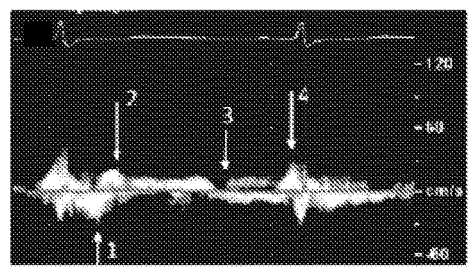
FIG. 12A        FIG. 12B
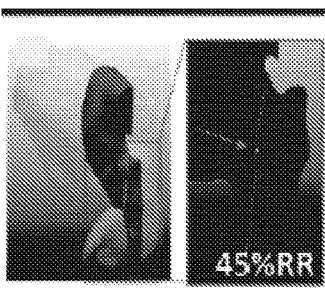 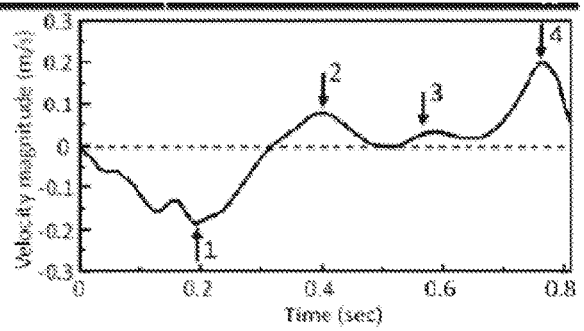
FIG. 12C        FIG. 12D
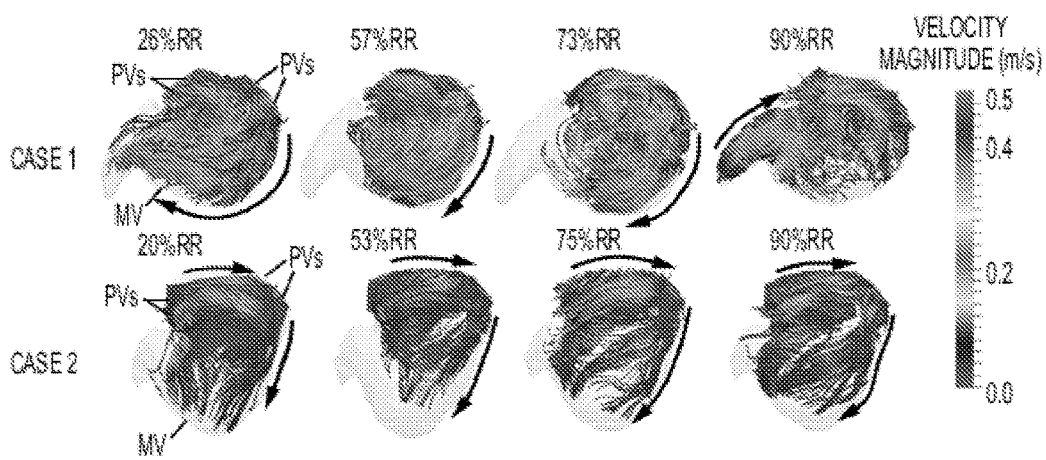
FIG. 13

PATIENT-SPECIFIC VIRTUAL INTERVENTION LABORATORY TO PREVENT STROKE

CROSS-REFERENCE TO RELATED APPLICATIONS

This application is a 35 U.S.C. § 371 U.S. national entry of International Application PCT/US2016/028435, having an international filing date of Apr. 20, 2016, which claims the benefit of U.S. Provisional Application No. 62/150,157, filed Apr. 20, 2015, and U.S. Provisional Application No. 62/258,353, filed Nov. 20, 2015, the content of each of the aforementioned applications is herein incorporated by reference in their entirety.

BACKGROUND

1. Field of Invention

The field of the currently claimed embodiments of this invention relates to methods and systems for performing a personalized blood flow analysis in a left atrium of a subject.

2. Discussion of Related Art

Atrial fibrillation (AF) is the most common heart rhythm disorder in human beings, and is an enormous public health burden. AF currently impacts the lives of over 6 million Americans, and the prevalence is expected to increase to 12 million by 2050. At 40 years of age, remaining lifetime risks for AF are as high as 26%. Most importantly, AF is associated with an increased risk of stroke. AF accounts for one in four strokes in those aged 80 years or older. AF is also associated with a five-fold increase in risk of stroke, and accounts for 15% of all strokes in the U.S. Stroke risk persists in patients with asymptomatic or subclinical AF. Moreover, AF is associated with a two-fold increased risk of dementia, and as high as 10% of AF patients develop dementia over 5 years.

The current standard of care to reduce the risk of stroke in patients with AF is oral anticoagulation (AC), which is a blood thinner to prevent blood clot formation. Since stroke actually occurs in only a minority of AF patients, whereas AC-related bleeding risk markedly increases with age, accurate assessment of stroke risk in individual patients is of critical importance. The current paradigm to estimate the risk of AF-related stroke is the CHA2DS2-VASC scoring system based on age, sex and comorbidities, and AC is recommended for those with a CHA2DS2-VASC score of 2 or greater. However, as many as 12% of those with a score of 0 or 1, who wouldn't be indicated for AC, can develop thrombi in the left atrial appendage (LAA), which is the most common site of intracardiac thrombus. In addition, as many as 14% of those with a score of 1 can develop stroke over a five year period. Furthermore, the CHA2DS2-VASC system is powerless against subclinical AF, where stroke can be the first manifestation of AF. Recently, the patients with AF are just beginning to have percutaneous options to reduce the risk of stroke by occluding the LAA. At this point, the indication for LAA closure devices is limited typically to patients who cannot tolerate AC for a history or a risk of bleeding complications. However, there is a possibility that a larger number of patients would benefit from the LAA closure rather than AC given the risk/benefit ratio. Finally, rhythm control approaches including drugs and catheter ablation are also available to reduce AF burden. However, at this point the impact of rhythm control approaches to the risk of cerebrovascular events is unclear. Clearly, there is an urgent need for an improved risk-stratification paradigm to guide personalized therapy to prevent AF-related cerebrovascular events.

SUMMARY

Some embodiments of the invention are directed towards a method of performing a computerized cardiac simulation for at least one of diagnosis, risk assessment or treatment planning, including: receiving, by a computer, a plurality of three-dimensional cardiac images of a subject's heart such that each three-dimensional cardiac image corresponds to a different phase of a single cardiac cycle of the subject's heart; modeling structure, using the computer, of the left atrium of the subject as a function of time using the plurality of three-dimensional cardiac images of the subject's heart; modeling blood flow, using the computer, within, into and out of the left atrium of the subject as a function of time using computational fluidic dynamics and using structure of said left atrium obtained from at least one of said plurality of three-dimensional cardiac images or said modeling structure of said left atrium; simulating at least one of time dependent structural function or time-dependent blood flow of said left atrium using results from said modeling structure and said modeling blood flow for a selected period of time; and providing information to a user from said simulating for use in at least one of diagnosis, risk assessment or treatment planning for a physiological effect related to function of said left atrium of said subject.

Some embodiments of the invention are directed towards a system for performing a computerized cardiac simulation for at least one of diagnosis, risk assessment or treatment planning, comprising a processor, wherein the processor is configured to receive a plurality of three-dimensional cardiac images of a subject's heart such that each three-dimensional cardiac image corresponds to a different phase of a single cardiac cycle of the subject's heart, wherein the processor is configured to generate a model structure of the left atrium of the subject as a function of time using the plurality of three-dimensional cardiac images of the subject's heart, wherein the processor is configured to generate a model of blood flow within, into and out of the left atrium of the subject as a function of time using computational fluidic dynamics and using structure of the left atrium obtained from at least one of the plurality of three-dimensional cardiac images or the model structure of the left atrium, wherein the processor is configured to generate a simulation of at least one of time dependent structural function or time-dependent blood flow of the left atrium using results from the model structure and the model of blood flow for a selected period of time, and wherein the processor is configured to provide information to a user from the simulation for use in at least one of diagnosis, risk assessment or treatment planning for a physiological effect related to function of the left atrium of the subject.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising: receiving, by a computer, a plurality of three-dimensional cardiac images of a subject's heart such that each three-dimensional cardiac image corresponds to a different phase of a single cardiac cycle of the subject's heart; modeling structure, using the computer, of the left atrium of the subject as a function of time using the plurality of three-dimensional cardiac images of the subject's heart; modeling blood flow, using the computer, within, into and out of the left atrium of the subject as a function of time using computational fluidic dynamics and using structure of the left atrium obtained from at least one of the plurality of three-dimensional cardiac images or the modeling structure of the left atrium; simulating at least one of time dependent structural function or time-dependent blood flow of the left atrium using results from the modeling structure and the modeling blood flow for a selected period of time; and providing information to a user from the simulating for use in at least one of diagnosis, risk assessment or treatment planning for a physiological effect related to function of the left atrium of the subject.

Some embodiments of the invention are directed towards a system for performing a computerized cardiac simulation for at least one of diagnosis, risk assessment or treatment planning, including: a processor; and a noninvasive imaging modality in communication with the processor, wherein the processor is configured to receive a plurality of three-dimensional cardiac images of a subject's heart such that each three-dimensional cardiac image corresponds to a different phase of a single cardiac cycle of the subject's heart, wherein the processor is configured to generate a model structure of the left atrium of the subject as a function of time using the plurality of three-dimensional cardiac images of the subject's heart, wherein the processor is configured to generate a model of blood flow within, into and out of the left atrium of the subject as a function of time using computational fluidic dynamics and using structure of the left atrium obtained from at least one of the plurality of three-dimensional cardiac images or the model structure of the left atrium, wherein the processor is configured to generate a simulation of at least one of time dependent structural function or time-dependent blood flow of the left atrium using results from the model structure and the model of blood flow for a selected period of time, and wherein the processor is configured to provide information to a user from the simulation for use in at least one of diagnosis, risk assessment or treatment planning for a physiological effect related to function of the left atrium of the subject.

BRIEF DESCRIPTION OF THE DRAWINGS

Further objectives and advantages will become apparent from a consideration of the description, drawings, and examples.

FIG. 12A shows TEE images of the left atrial appendage (LAA) (90° angle). The arrow shows the sampling point of the velocity magnitude measurements along the dashed line from bottom to top of the image; FIG. 12B shows a graph of a time course of flow velocity magnitude by pulsed-Doppler TEE tracing; FIG. 12C shows a schematic of corresponding sampling point and direction along which to measure the flow velocity magnitude in the CFD results; FIG. 12D shows a graph showing a time course of flow velocity magnitude from the CFD results.

FIG. 13 shows models showing streamlines of blood flow during a representative cardiac cycle in the posterior view. Top row shows case 1; Bottom row shows case 2.

DETAILED DESCRIPTION

Figure 1A:
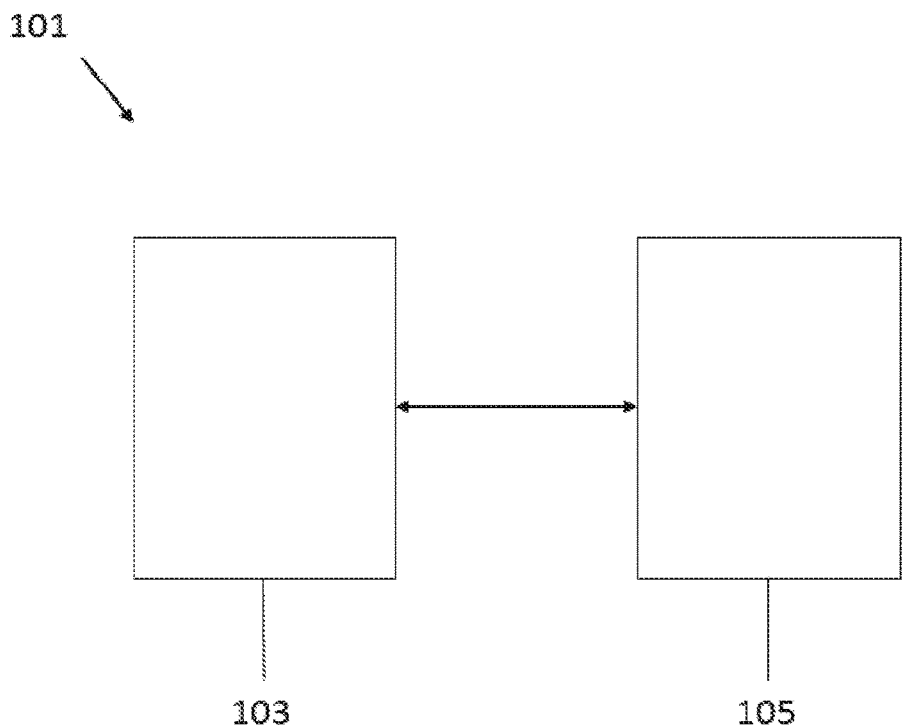
FIG. 1A is a diagram of a system per an embodiment of the invention.

Some embodiments of the current invention are discussed in detail below. In describing embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification, including the Background and Detailed Description sections, are incorporated by reference as if each had been individually incorporated.

The term "subject" refer to a particular person or animal, i.e., an individual, and not a generic, standard or idealized person or individual. In other words, the simulations are personalized.

A computing device may perform certain functions in response to processor executing software instructions contained in a computer-readable medium, such as a memory. In alternative embodiments, hardwired circuitry may be used in place of or in combination with software instructions to implement features consistent with principles of the disclosure. Thus, implementations consistent with principles of the disclosure are not limited to any specific combination of hardware circuitry and software.

Exemplary embodiments may be embodied in many different ways as a software component. For example, it may be a stand-alone software package, a combination of software packages, or it may be a software package incorporated as a "tool" in a larger software product. It may be downloadable from a network, for example, a website, as a stand-alone product or as an add-in package for installation in an existing software application. It may also be available as a client-server software application, or as a web-enabled software application. It may also be embodied as a software package installed on a hardware device such as a CT or MRI scanner, for example.

Recent evidence suggests that left atrial (LA) dysfunction may be mechanistically contributing to cerebrovascular events in patients with atrial fibrillation (AF). Some embodiments of the instant invention relate to methods and systems for performing a personalized blood flow analysis in a left atrium of a subject. Other embodiments of the instant invention evaluate the association between regional LA function and a prior history of stroke during sinus rhythm in patients referred for catheter ablation of AF.

Some embodiments of the invention are directed towards a method of performing a computerized cardiac simulation for at least one of diagnosis, risk assessment or treatment planning, including: receiving, by a computer, a plurality of three-dimensional cardiac images of a subject's heart such that each three-dimensional cardiac image corresponds to a different phase of a single cardiac cycle of the subject's heart; modeling structure, using the computer, of the left atrium of the subject as a function of time using the plurality of three-dimensional cardiac images of the subject's heart; modeling blood flow, using the computer, within, into and out of the left atrium of the subject as a function of time using computational fluidic dynamics and using structure of said left atrium obtained from at least one of said plurality of three-dimensional cardiac images or said modeling structure of said left atrium; simulating at least one of time dependent structural function or time-dependent blood flow of said left atrium using results from said modeling structure and said modeling blood flow for a selected period of time; and providing information to a user from said simulating for use in at least one of diagnosis, risk assessment or treatment planning for a physiological effect related to function of said left atrium of said subject.

Some embodiments of the invention are directed towards a method of performing a computerized cardiac simulation for at least one of diagnosis, risk assessment or treatment planning, including obtaining a plurality of three-dimensional cardiac images of a subject's heart from a noninvasive imaging modality.

Some embodiments of the invention are directed towards a method of performing a computerized cardiac simulation for at least one of diagnosis, risk assessment or treatment planning, including obtaining a plurality of three-dimensional cardiac images of a subject's heart from at least one of CT, MRI, PET, SPECT, or ultrasound imaging.

Some embodiments of the invention are directed towards a method of performing a computerized cardiac simulation for at least one of diagnosis, risk assessment or treatment planning, including obtaining a plurality of three-dimensional cardiac images of a subject's heart from at least five three-dimensional cardiac images within a single cardiac cycle.

Some embodiments of the invention are directed towards a method of performing a computerized cardiac simulation for at least one of diagnosis, risk assessment or treatment planning, including obtaining a plurality of three-dimensional cardiac images of a subject's heart from at least twenty three-dimensional cardiac images within a single cardiac cycle.

Some embodiments of the invention are directed towards a method of performing a computerized cardiac simulation for at least one of diagnosis, risk assessment or treatment planning, including providing information to a user from a simulation wherein information provides information for use in at least one of a diagnosis or risk assessment for stroke or dementia.

Some embodiments of the invention are directed towards a method of performing a computerized cardiac simulation for at least one of diagnosis, risk assessment or treatment planning, including providing information in a form of a three dimensional map. In some embodiments, this three-dimensional map is a dynamic map that changes in time in correspondence to the selected period of time of the simulating.

Some embodiments of the invention are directed towards a method of performing a computerized cardiac simulation for at least one of diagnosis, risk assessment or treatment planning, including providing information on at least one of a residual blood flow in the left atrium and/or a left atrial appendage, shear rate on a left atrial wall, vortex formation in the left atrium, blood flow across a mitral valve, changes in volume of a left ventricle, blood flow in a pulmonary vein, and blood flow across an aortic valve.

Some embodiments of the invention are directed towards a method of performing a computerized cardiac simulation for at least one of diagnosis, risk assessment or treatment planning, including modeling blood flow including adding effects of one or more administered compound designed to change a fluid property of the blood.

Some embodiments of the invention are directed towards a method of performing a computerized cardiac simulation for at least one of diagnosis, risk assessment or treatment planning, including modeling structure and modeling blood flow, wherein at least one of the modeling structure or the modeling blood flow includes adding effects of at least one planned or actual treatment.

Some embodiments of the invention are directed towards a method of performing a computerized cardiac simulation for at least one of diagnosis, risk assessment or treatment planning, including modeling structure and modeling blood flow, wherein at least one of the modeling structure or the modeling blood flow includes adding effects based on empirical data from the subject.

Some embodiments of the invention are directed towards a method of performing a computerized cardiac simulation for at least one of diagnosis, risk assessment or treatment planning, including acquiring a plurality of three-dimensional cardiac images with a resolution of at least 2 mm.

Some embodiments of the invention are directed towards a system for performing a computerized cardiac simulation for at least one of diagnosis, risk assessment or treatment planning, comprising a processor, wherein the processor is configured to receive a plurality of three-dimensional cardiac images of a subject's heart such that each three-dimensional cardiac image corresponds to a different phase of a single cardiac cycle of the subject's heart, wherein the processor is configured to generate a model structure of the left atrium of the subject as a function of time using the plurality of three-dimensional cardiac images of the subject's heart, wherein the processor is configured to generate a model of blood flow within, into and out of the left atrium of the subject as a function of time using computational fluidic dynamics and using structure of the left atrium obtained from at least one of the plurality of three-dimensional cardiac images or the model structure of the left atrium, wherein the processor is configured to generate a simulation of at least one of time dependent structural function or time-dependent blood flow of the left atrium using results from the model structure and the model of blood flow for a selected period of time, and wherein the processor is configured to provide information to a user from the simulation for use in at least one of diagnosis, risk assessment or treatment planning for a physiological effect related to function of the left atrium of the subject.

Some embodiments of the invention are directed towards a system for performing a computerized cardiac simulation for at least one of diagnosis, risk assessment or treatment planning, comprising a processor and further comprising a noninvasive imaging modality in communication with the processor.

Some embodiments of the invention are directed towards a system for performing a computerized cardiac simulation for at least one of diagnosis, risk assessment or treatment planning, comprising a processor and further comprising an imaging system in communication with the processor, wherein the imaging system is configured to perform at least one of CT, MRI, PET, SPECT, or ultrasound imaging.

Some embodiments of the invention are directed towards a system for performing a computerized cardiac simulation for at least one of diagnosis, risk assessment or treatment planning, comprising a processor, wherein the processor is configured to receive a plurality of three-dimensional cardiac images of the subject's heart of at least five three-dimensional cardiac images within a single cardiac cycle.

Some embodiments of the invention are directed towards a system for performing a computerized cardiac simulation for at least one of diagnosis, risk assessment or treatment planning, comprising a processor configured to receive a plurality of three-dimensional cardiac images of the subject's heart of at least twenty three-dimensional cardiac images within a single cardiac cycle.

Some embodiments of the invention are directed towards a system for performing a computerized cardiac simulation for at least one of diagnosis, risk assessment or treatment planning, comprising a processor, wherein the processor is further configured to provide information to a user for use in at least one of a diagnosis or risk assessment for stroke or dementia.

Some embodiments of the invention are directed towards a system for performing a computerized cardiac simulation for at least one of diagnosis, risk assessment or treatment planning, comprising a processor, wherein the processor is further configured to provide information to a user from a simulation in a form of a three dimensional map. In some embodiments, this three-dimensional map is a dynamic map that changes in time in correspondence to a selected period of time of a simulation.

Some embodiments of the invention are directed towards a system for performing a computerized cardiac simulation for at least one of diagnosis, risk assessment or treatment planning, comprising a processor, wherein the processor is further configured to provide information to a user including at least one of a residual blood flow in the left atrium and/or a left atrial appendage, shear rate on a left atrial wall, vortex formation in the left atrium, blood flow across a mitral valve, changes in volume of a left ventricle, blood flow in a pulmonary vein, and blood flow across an aortic valve from the simulating.

Some embodiments of the invention are directed towards a system for performing a computerized cardiac simulation for at least one of diagnosis, risk assessment or treatment planning, comprising a processor, wherein the processor is configured to generate a model of blood flow including adding effects of one or more administered compound designed to change a fluid property of blood.

Some embodiments of the invention are directed towards a system for performing a computerized cardiac simulation for at least one of diagnosis, risk assessment or treatment planning, comprising a processor, wherein the processor is further configured to at least one of generate a model structure including adding effects of at least one planned or actual treatment or generate a model of blood flow including adding effects of at least one planned or actual treatment.

Some embodiments of the invention are directed towards a system for performing a computerized cardiac simulation for at least one of diagnosis, risk assessment or treatment planning, comprising a processor, wherein the processor is further configured to at least one of generate a modeling structure including adding effects based on empirical data from the subject or generate a model of blood flow including adding effects based on empirical data from the subject.

Some embodiments of the invention are directed towards a system for performing a computerized cardiac simulation for at least one of diagnosis, risk assessment or treatment planning, comprising a processor, wherein the processor is further configured to receive a plurality of three-dimensional cardiac images having a resolution of at least 2 mm.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising: receiving, by a computer, a plurality of three-dimensional cardiac images of a subject's heart such that each three-dimensional cardiac image corresponds to a different phase of a single cardiac cycle of the subject's heart; modeling structure, using the computer, of the left atrium of the subject as a function of time using the plurality of three-dimensional cardiac images of the subject's heart; modeling blood flow, using the computer, within, into and out of the left atrium of the subject as a function of time using computational fluidic dynamics and using structure of the left atrium obtained from at least one of the plurality of three-dimensional cardiac images or the modeling structure of the left atrium; simulating at least one of time dependent structural function or time-dependent blood flow of the left atrium using results from the modeling structure and the modeling blood flow for a selected period of time; and providing information to a user from the simulating for use in at least one of diagnosis, risk assessment or treatment planning for a physiological effect related to function of the left atrium of the subject.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising receiving a plurality of three-dimensional cardiac images of a subject's heart from a noninvasive imaging modality.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising receiving a plurality of three-dimensional cardiac images of a subject's heart from at least one of CT, MRI, PET, SPECT, or ultrasound imaging.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising receiving a plurality of three-dimensional cardiac images of a subject's heart from at least five three-dimensional cardiac images within a single cardiac cycle.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising receiving a plurality of three-dimensional cardiac images of a subject's heart from least twenty three-dimensional cardiac images within a single cardiac cycle.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising providing information to a user for use in at least one of a diagnosis or risk assessment for stroke or dementia.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising providing information in a form of a three dimensional map. In some embodiments, the three-dimensional map is a dynamic map that changes in time in correspondence to the selected period of time of the simulating.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising providing information to a user from a simulating wherein the information provides information including at least one of a residual blood flow in the left atrium and/or a left atrial appendage, shear rate on a left atrial wall, vortex formation in the left atrium, blood flow across a mitral valve, changes in volume of a left ventricle, blood flow in a pulmonary vein, and blood flow across an aortic valve.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising modeling blood flow including adding effects of one or more administered compound designed to change a fluid property of the blood.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising at least one of modeling structure or modeling blood flow includes adding effects of at least one planned or actual treatment.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising at least one of modeling structure or modeling blood flow includes adding effects based on empirical data from a subject.

Some embodiments of the invention are directed towards a computer readable medium comprising a non-transient computer readable program that upon execution by a processor causes the processor to perform a computerized cardiac simulation for at least one of diagnosis, risk assessment or treatment planning, comprising receiving a plurality of three-dimensional cardiac images have a resolution of at least 2 mm.

Some embodiments of the invention are directed towards a system for performing a computerized cardiac simulation for at least one of diagnosis, risk assessment or treatment planning, including: a processor; and a noninvasive imaging modality in communication with the processor, wherein the processor is configured to receive a plurality of three-dimensional cardiac images of a subject's heart such that each three-dimensional cardiac image corresponds to a different phase of a single cardiac cycle of the subject's heart, wherein the processor is configured to generate a model structure of the left atrium of the subject as a function of time using the plurality of three-dimensional cardiac images of the subject's heart, wherein the processor is configured to generate a model of blood flow within, into and out of the left atrium of the subject as a function of time using computational fluidic dynamics and using structure of the left atrium obtained from at least one of the plurality of three-dimensional cardiac images or the model structure of the left atrium, wherein the processor is configured to generate a simulation of at least one of time dependent structural function or time-dependent blood flow of the left atrium using results from the model structure and the model of blood flow for a selected period of time, and wherein the processor is configured to provide information to a user from the simulation for use in at least one of diagnosis, risk assessment or treatment planning for a physiological effect related to function of the left atrium of the subject.

FIG. 1A shows a conceptual model of an embodiment of the invention. More specifically, FIG. 1A is a system for performing a computerized cardiac simulation for at least one of diagnosis, risk assessment or treatment planning 101 having a processor 103 and a noninvasive imaging modality 105 in communication with the processor.

Figure 1B:
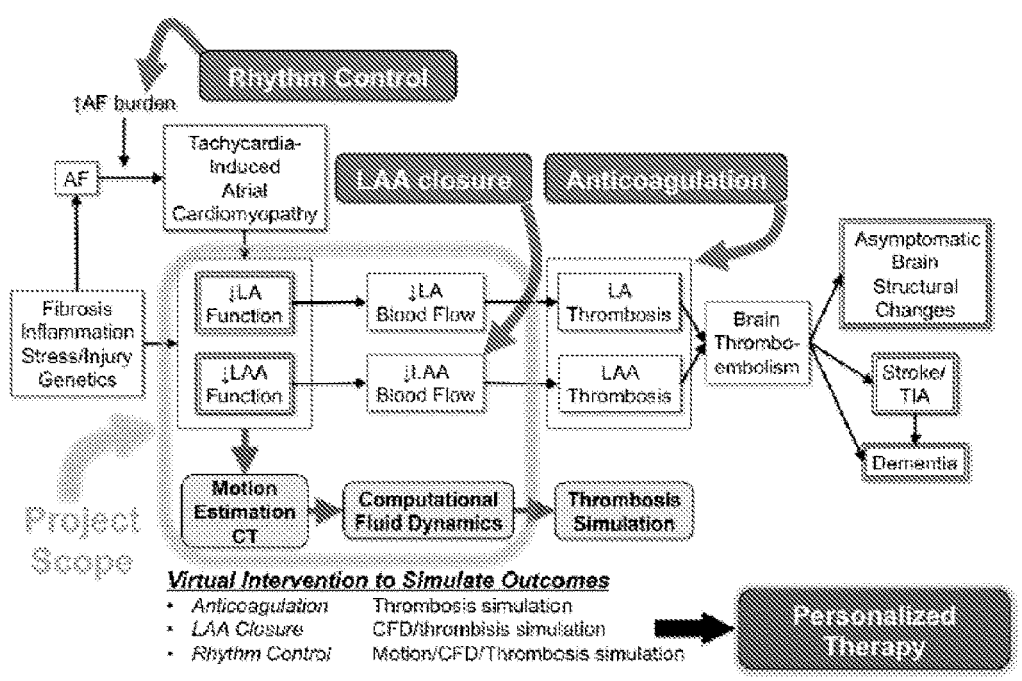
FIG. 1B is a schematic of a conceptual model of atrial fibrillation, atrial function and cerebrovascular events.

FIG. 1B shows a conceptual model of an embodiment of the invention. In FIG. 1B, LA=left atrium; LAA=left atrial appendage; CT=computed tomography; CFD=computational fluid dynamics; TIA=transient ischemic attack. A long-term goal of certain embodiments of the instant invention is to develop a cloud application ("app") to recommend simulation-guided personalized therapy to prevent cerebrovascular events associated with AF. This app can be distributed to medical imaging vendors, standalone imaging centers and executive health screening services to help individual AF patients make an informed decision by providing a better risk/benefit calculation of prophylactic interventions such as AC, LAA closure, or rhythm control approaches in patients with AF. The predictive value of the app can continuously be improved by incorporating the results from clinical outcome studies as they become available. An embodiment of the invention can will utilize an image-based simulation platform to assess the risk of cerebrovascular events, such as stroke, TIA and dementia, based on the specific patient heart anatomy and function. Embodiments can use high-resolution, 3-D motion estimation CT to acquire patient-specific LA regional wall motion, and will apply computational fluid dynamics (CFD) to simulate 3-D blood flow within the LA and the LAA. Embodiments can also perform thrombosis simulation based on CFD simulation to identify the potential risk and the site(s) of blood clot formation within the heart. An advantage of certain embodiments of the instant invention can allow virtual interventions to simulate outcomes based on patient-specific anatomy and function. This is can be a value that certain embodiments of the instant invention offer beyond the existing medical imaging technologies, including CT, MRI and echocardiography. Embodiments of the instant invention can overcome the limitations associated with the current paradigm, and justify screening and more effective prophylactic interventions in patients at a higher risk, while avoiding the complications and the cost of interventions in lower-risk individuals.

Certain embodiments of the instant invention include a prototype of an app that allows virtual LAA closure procedures in individual patients. In this case, computational fluid dynamics (CFD) simulation based on patient-specific heart anatomy and function derived from a motion-estimation CT can be used to estimate LA blood flow before and after LAA closure.

The following examples describe some embodiments and some applications in more detail. However, the broad concepts of the current invention are not limited to the particular examples.

EXAMPLES

Example 1

Atrial fibrillation (AF)—the most common arrhythmia—affects 6 million individuals in the United States. AF is associated with an increased risk of stroke[1,2] that can be fatal, and survivors are often left permanently disabled. Mechanistically, cerebrovascular events in AF patients are thought to result from ineffective contraction during AF which result in subsequent intracardiac thrombosis. However, recent evidence suggests that underlying atrial fibrosis and subsequent atrial dysfunction may also be mechanistically contributing to cerebrovascular events in AF patients. For example, an increased left atrial (LA) volume[3] and global LA dysfunction in individuals without clinically recognized AF are an independent predictor of clinical stroke/transient ischemic attack (TIA)[4] as well as subclinical cerebrovascular events detected by brain MRI[5]. Previous studies have demonstrated that the degree of regional LA dysfunction during sinus rhythm is proportional to the extent of underlying fibrosis quantified by late gadolinium enhancement (LGE) of cardiac magnetic resonance (CMR) in AF patients[6]. In addition, regional LA function during AF is significantly depressed in patients with a prior history of stroke compared with those without, independent of the CHA2DS2-VASc score[7,8], the standard system of risk stratification for stroke based on age, sex, and comorbidities[9].

To further support the hypothesis that the underlying atrial fibrosis and subsequent LA dysfunction may be mechanistically contributing to cerebrovascular events in AF patients, embodiments of the instant invention investigated the association between regional LA function and a prior history of stroke during sinus rhythm in patients referred for catheter ablation of AF. In certain embodiments, tissue-tracking CMR[10,11] was used to quantify the LA volume and regional LA function.

Results

A total of 169 patients (59±10 years, 74% male, 29% persistent AF) with a history of AF in sinus rhythm at the time of pre-ablation cardiac magnetic resonance (CMR) were analyzed. The LA volume, emptying fraction (EF), strain (S), and strain rate (SR) were assessed by tissue-tracking CMR. The patients with a history of stroke or transient ischemic attack (TIA) (n=18) had greater LA volumes ($V_{max}$ and $V_{min}$; p=0.02 and p<0.001, respectively), lower LA total EF (p<0.001), lower LA maximum and pre-atrial contraction strains ($S_{max}$ and $S_{preA}$; p<0.001 and p=0.01, respectively), and lower absolute values of LA SR during left ventricular (LV) systole and early diastole ($SR_s$ and $SR_e$; p=0.005 and p=0.03, respectively) than those without stroke/TIA (n=151). Multivariable analysis demonstrated that the lower LA reservoir function, including total EF, $S_{max}$, and $SR_s$, was associated with stroke/TIA (OR 0.94, 0.91, and 0.17; p=0.03, 0.02, and 0.04, respectively) after adjusting for the CHA2DS2-VASc score and LA $V_{min}$.

The data show that depressed LA reservoir function as assessed by tissue-tracking CMR is significantly associated with a prior history of stroke/TIA in patients with AF. Thus, assessment of LA reservoir function can improve the risk stratification of cerebrovascular events in AF patients.

With the large number of possible treatment options available for AF patients, it is desirable to have a rational and non-invasive method for selecting treatment options that minimize the dangers of cerebrovascular events while minimizing costs and patient risk. The method and data set developed herein show that LA reservoir function and particularly LA strain and strain rate are related to cerebrovascular events. While the risk prediction demonstrated herein is in itself useful, the method and data set are being used to construct a model la function. This model can then be informed with actual CMR measurement of a specific patient thereby creating a virtual patient representative of that patient. Not only does this model output the initial cerebrovascular risk factors, it also responds to various treatment options such as occlusion of the LAA. This virtual patient model allows the clinician to try a variety of single or of combined treatments for AF and determine which treatment or set of treatments results in the most favorable cerebrovascular event outcome.

Patient Demographics.

Clinical characteristics of the patients are summarized in Table 1. A total of 169 patients (59±10 years, 74% male, 29% persistent AF) were included in the analysis. Compared to the control group, patients in the stroke group were significantly older (p=0.02). Other clinical characteristics, including the $CHADS_2$ score and $CHA_2DS_2$-VASc scores, did not show any significant difference between the stroke and control groups. Three of 18 patients (16.7%) in the stroke group and 18 of 151 patients (11.9%) in the control group underwent cardioversion before pre-ablation CMR (p=0.84). There was no significant difference in AF duration before cardioversion (3.3±3.2 vs. 1.2±1.3 years, p=0.15) and the time from cardioversion to CMR (59.7±42.7 vs. 52.2±42.7 days, p=0.80).

TABLE 1

Patient demographics

|  | Stroke (n = 18) | Control (n = 151) | p value |
|---|---|---|---|
| Age (years) | 65.0 ± 8.2 | 58.5 ± 10.6 | 0.02* |
| Sex (male) | 12 (66.7) | 113 (74.8) | 0.50 |
| Body mass index (kg/m$^2$) | 27.8 ± 2.4 | 28.0 ± 5.3 | 0.94 |
| Type of AF (persistent) | 5 (27.8) | 44 (29.1) | 0.91 |
| Coronary artery disease | 4 (22.2) | 16 (10.6) | 0.14 |
| Hypertension | 7 (38.9) | 60 (39.7) | 0.94 |
| Heart failure | 2 (11.1) | 12 (7.9) | 0.63 |
| Diabetes mellitus | 3 (16.7) | 18 (11.9) | 0.55 |
| $CHADS_2$ score before stroke | 0.94 ± 0.90 | 0.74 ± 0.90 | 0.20 |
| $CHA_2DS_2$-VASc score before stroke | 2.00 ± 1.32 | 1.45 ± 1.49 | 0.07 |
| Medications |  |  |  |
| β-blockers | 10 (55.5) | 73 (48.3) | 0.70 |
| Ca channel blockers | 6 (33.3) | 33 (21.9) | 0.44 |
| ACE inhibitors/ARBs | 6 (33.3) | 49 (32.5) | 0.96 |
| Statins | 7 (38.9) | 62 (41.1) | 0.86 |
| Number of antiarrhythmic drugs | 1.4 ± 0.9 | 1.6 ± 0.9 | 0.60 |

In Table 1, data are expressed as the means ± standard deviations, or as n (%).
ACE, Angiotensin-converting enzyme;
AF, atrial fibrillation;
ARB, angiotensin receptor blocker.
*p < .05.

LA Function and Stroke.

Figure 4:
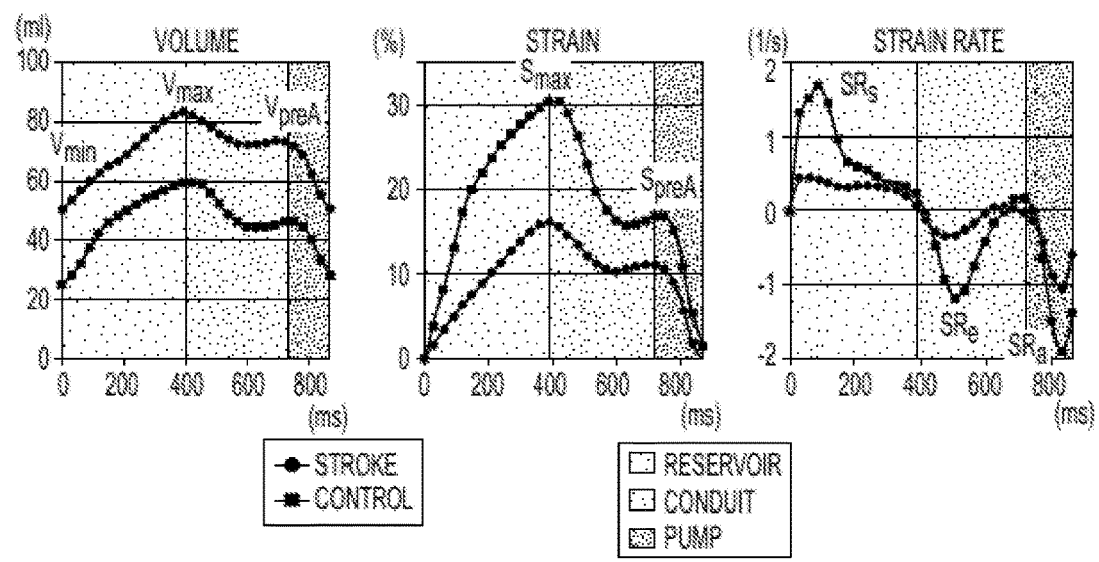
FIG. 4 shows graphs showing LA measurements by tissue-tracking CMR in patients with and without stroke.

The time course of LA volume, strain, and strain rate in representative patients with and without stroke are shown in FIG. 4. The CMR parameters in the stroke and the control groups are shown in Table 2. In the stroke group, the LA volumes ($V_{max}$, $V_{preA}$, and $V_{min}$) were significantly higher, the LA EFs (total, passive, and active) were lower, the LA longitudinal $S_{max}$ and $S_{preA}$ were lower, and the absolute values of the LA $SR_s$ and $SR_e$ were lower than in the control group. There was no significant difference regarding LA wall LGE between the two groups (stroke group vs. control group: 29.3±17.6 vs. 27.1±16.1%, respectively, p=0.75). LV parameters, including mass index, ejection fraction, end-diastolic volume index, and longitudinal strain, did not show any significant difference between the stroke and control groups.

FIG. 4 shows LA Measurements by Tissue-Tracking CMR in Patients with and without Stroke. (A) The LA volume, (B) LA global longitudinal strain, and (C) LA strain rate in a patient with stroke (red line) and without stroke (blue line). The patient with stroke has a larger LA volume and smaller strain and strain rate. The LA serves as a reservoir during LV systole, as a conduit during LV early diastole, and as an active pump during late diastole. The abbreviations are as in FIGS. 2 and 3.

TABLE 2

Comparison of CMR measurements between the stroke and control groups

|  | Stroke (n = 18) | Control (n = 151) | p value |
|---|---|---|---|
| LA $V_{max}$ (ml/m$^2$) | 52.2 ± 16.2 | 44.2 ± 12.9 | 0.024* |
| LA $V_{preA}$ (ml/m$^2$) | 44.8 ± 14.5 | 35.7 ± 11.7 | 0.005* |
| LA $V_{min}$ (ml/m$^2$) | 35.1 ± 15.8 | 24.6 ± 10.7 | <0.001* |
| LA total EF (%) | 34.6 ± 13.5 | 45.6 ± 11.8 | <0.001* |
| LA passive EF (%) | 14.1 ± 5.6 | 19.7 ± 7.8 | 0.005* |
| LA active EF (%) | 23.8 ± 15.8 | 32.7 ± 10.9 | 0.004* |
| LA $S_{max}$ (%) | 19.4 ± 9.2 | 28.6 ± 10.6 | <0.001* |
| LA $S_{preA}$ (%) | 10.1 ± 6.6 | 15.0 ± 7.1 | 0.010* |
| LA $SR_s$ (1/s) | 0.81 ± 0.37 | 1.15 ± 0.47 | 0.005* |
| LA $SR_e$ (1/s) | −0.78 ± 0.41 | −1.12 ± 0.62 | 0.033* |
| LA $SR_a$ (1/s) | −1.14 ± 0.55 | −1.52 ± 0.84 | 0.071 |
| LV mass index (g/m$^2$) | 71.0 ± 16.1 | 65.6 ± 14.6 | 0.177 |
| LV ejection fraction (%) | 54.4 ± 14.6 | 57.3 ± 9.5 | 0.281 |
| LV end-diastolic volume index (ml/m$^2$) | 78.7 ± 26.7 | 71.7 ± 12.4 | 0.292 |
| LV longitudinal strain (%) | −16.5 ± 5.2 | −18.2 ± 4.4 | 0.149 |

In Table 2, data are expressed as the means ± standard deviations.
CMR, cardiovascular magnetic resonance;
EF, emptying fraction;
LA, left atrial;
LV, left ventricular;
$S_{max}$, maximum strain;
$S_{preA}$, pre-atrial contraction strain;
$SR_a$, strain rate at atrial contraction;
$SR_e$, strain rate at LV early diastole;
$SR_s$, maximum strain rate;
$V_{max}$, maximum indexed volume;
$V_{min}$, minimum indexed volume;
$V_{preA}$, pre-atrial contraction indexed volume.
*p < .05.

Univariable and Multivariable Analyses.

The univariable and multivariable analyses regarding the association between the CMR-measured parameters and stroke are summarized in Table 3. In Model 1, a univariable analysis identified larger LA volumes ($V_{max}$, $V_{preA}$, and $V_{min}$), lower EFs (total, active, and passive EF), lower strains ($S_{max}$ and $S_{preA}$), and lower absolute values of SR ($SR_s$ and $SR_e$) as significant contributors to stroke, indicating that all of the LA parameters that differed significantly between the stroke and control groups in Table 2 remained significant and were associated with stroke. In Model 2, larger $V_{preA}$ and $V_{min}$, lower EFs (total, active, and passive EF), lower strains ($S_{max}$ and $S_{preA}$), and lower $SR_s$ were significantly associated with stroke after adjusting for the $CHA_2DS_2$-VASc score. In Model 3, only the LA total EF, $S_{max}$, and $SR_s$, which reflect the LA reservoir function (FIGS. 3 and 4), remained significant after additionally adjusting for the LA $V_{min}$.

TABLE 3

Univariable and multivariable analyses of the associations between CMR measurements and stroke

|  | Model 1 | | Model 2 | | Model 3 | |
| --- | --- | --- | --- | --- | --- | --- |
|  | OR (95% CI) | p value | OR (95% CI) | p value | OR (95% CI) | p value |
| LA $V_{max}$ | 1.04 (1.01-1.08) | 0.030* | 1.04 (0.99-1.08) | 0.062 | ... | |
| LA $V_{preA}$ | 1.06 (1.02-1.10) | 0.008* | 1.05 (1.01-1.10) | 0.019* | ... | |
| LA $V_{min}$ | 1.07 (1.03-1.11) | 0.002* | 1.06 (1.02-1.11) | 0.005* | ... | |
| LA total EF | 0.93 (0.89-0.97) | 0.002* | 0.93 (0.89-0.97) | 0.002* | 0.94 (0.89-0.99) | 0.030* |
| LA passive EF | 0.89 (0.81-0.96) | 0.007* | 0.89 (0.81-0.96) | 0.020* | 0.92 (0.83-1.00) | 0.063 |
| LA active EF | 0.94 (0.90-0.98) | 0.006* | 0.94 (0.90-0.98) | 0.008* | 0.96 (0.91-1.00) | 0.074 |
| LA $S_{max}$ | 0.90 (0.83-0.96) | 0.002* | 0.90 (0.83-0.95) | 0.002* | 0.91 (0.84-0.97) | 0.018* |
| LA $S_{preA}$ | 0.89 (0.80-0.97) | 0.012* | 0.89 (0.80-0.97) | 0.016* | 0.92 (0.82-1.01) | 0.091 |
| LA $SR_s$ | 0.10 (0.02-0.44) | 0.006* | 0.11 (0.02-0.50) | 0.009* | 0.17 (0.02-0.94) | 0.042* |
| LA $SR_e$ | 3.11 (1.14-8.72) | 0.039* | 2.88 (1.04-9.69) | 0.055 | 2.21 (0.72-7.49) | 0.175 |
| LA $SR_a$ | 2.21 (1.02-5.50) | 0.066 | 2.08 (0.94-5.24) | 0.095 | 1.48 (0.66-3.94) | 0.391 |
| LV mass index | 1.03 (0.99-1.06) | 0.189 | 1.02 (0.98-1.06) | 0.224 | 1.02 (0.98-1.06) | 0.321 |
| LV ejection fraction | 0.98 (0.93-1.03) | 0.301 | 0.98 (0.93-1.03) | 0.347 | 0.98 (0.93-1.06) | 0.547 |
| LV EDVI | 1.02 (0.99-1.05) | 0.253 | 0.98 (0.95-1.01) | 0.262 | 0.98 (0.95-1.01) | 0.303 |
| LV longitudinal strain | 1.08 (0.97-1.21) | 0.151 | 1.07 (0.96-1.20) | 0.223 | 1.05 (0.94-1.18) | 0.399 |

In Table 3, CI = confidence interval; EDVI = end-diastolic volume index; OR = odds ratio.
Other abbreviations match those in Tables 2.
*p < 0.05.
Model 1: unadjusted.
Model 2: adjusted for CHA2DS2-VASc score.
Model 3: additionally adjusted for the LA $V_{min}$.

Incremental Value of LA Function as a Marker of Stroke.

Figure 5:
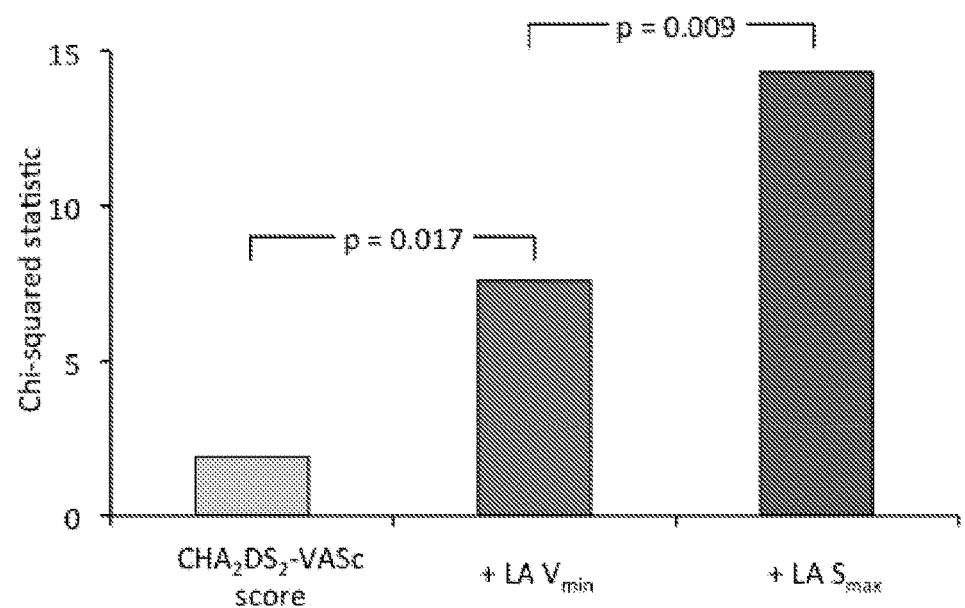
FIG. 5 shows a graph showing incremental value of LA strain for diagnosis of stroke.

Additionally, it was found that adding the CMR-measured LA function significantly improved the statistics of the model on the basis of the conventional risk stratification of strokes (FIG. 5). The LA $V_{min}$ provided incremental value over the $CHA_2DS_2$-VASc score, and the diagnostic value was further improved by adding the global LA $S_{max}$ (p=0.017 and 0.009, respectively).

FIG. 5 shows incremental Value of LA Strain for Diagnosis of Stroke. The addition of the LA minimum volume ($V_{min}$) to the model on the basis of the $CHA_2DS_2$-VASc score resulted in significant improvement in the diagnostic value for stroke. The value was further increased by adding the LA global longitudinal maximum strain ($S_{max}$).

Reproducibility of LA Analysis by Tissue-Tracking CMR.

The intra-observer ICC was between 0.88 and 0.99, and the inter-observer ICC was between 0.89 and 0.99 for all measured LA parameters from tissue-tracking CMR (Table 4).

TABLE 4

Reproducibility of the LA analysis by tissue-tracking CMR

|  | Intra-observer | | | Inter-observer | | |
| --- | --- | --- | --- | --- | --- | --- |
|  | Bias | Limits of agreement | ICC | Bias | Limits of agreement | ICC |
| LA $V_{max}$ (ml/m²) | −0.57 | 4.50 | 0.96 | −1.25 | 4.08 | 0.99 |
| LA $V_{preA}$ (ml/m²) | −0.93 | 3.42 | 0.97 | −0.34 | 4.75 | 0.99 |
| LA $V_{min}$ (ml/m²) | −0.83 | 3.68 | 0.98 | −1.61 | 4.31 | 0.98 |
| LA total EF (%) | 1.94 | 7.75 | 0.94 | 1.67 | 4.78 | 0.89 |
| LA passive EF (%) | 0.82 | 5.41 | 0.98 | −0.92 | 7.81 | 0.92 |
| LA active EF (%) | 2.47 | 10.78 | 0.88 | 3.11 | 0.51 | 0.90 |
| LA $S_{max}$ (%) | −0.75 | 3.19 | 0.94 | 1.26 | 2.88 | 0.90 |
| LA $S_{preA}$ (%) | −1.20 | 2.99 | 0.96 | 1.64 | 2.17 | 0.98 |
| LA $SR_s$ (1/s) | 0.10 | 0.43 | 0.91 | 0.11 | 0.18 | 0.95 |
| LA $SR_e$ (1/s) | −0.04 | 0.24 | 0.98 | −0.15 | 0.23 | 0.94 |
| LA $SR_a$ (1/s) | −0.05 | 0.28 | 0.99 | −0.12 | 0.27 | 0.97 |

In Table 4, CMR = cardiac magnetic resonance; ICC = intraclass correlation coefficient.
Other abbreviations match those in Table 2.

Discussion

Main Findings.

It was found that that greater LA volumes, lower LA EFs, lower peak strain, and lower peak SR were associated with a prior history of stroke. It was also found that LA total EF, LA $S_{max}$, and $SR_s$, representing the LA reservoir function, are independently associated with stroke or TIA after adjusting for potential confounders and clinical risk factors. These results are consistent with the previous reports that the reduced LA reservoir function accesses using transthoracic echocardiography in the absence of AF is an independent predictor of clinical stroke/TIA[4] as well as subclinical cerebrovascular events detected by brain MRI[5]. These findings are particularly important because this is the first report to demonstrate the significant contribution of the LA reservoir function to stroke in AF patients during sinus rhythm. In contrast to studies which showed a significant association between stroke and the LA reservoir function with echocardiography during AF[7, 8], the sinus rhythm in our study allows assessment of all the LA function components, including the reservoir function, conduit function, and booster pump function, and to successfully determine that only the LA reservoir function is significantly associated with stroke. This important finding further supports the concept that the underlying atrial fibrosis and subsequent LA dysfunction is mechanistically contributing to cerebrovascular events in AF patients.

Depressed LA Reservoir Function as a Mechanism of Thromboembolic Events in AF Patients.

The atrial function consists of three components: a reservoir function for pulmonary venous return during LV systole, the conduit function for pulmonary venous return during LV early diastole, and the booster pump function that augments LV filling during LV late diastole (FIG. 4). LA total EF, $S_{max}$, and $SR_s$ represent LA compliance and reservoir function, reflecting the passive stretch of the LA during LV systole. The mechanism as to how the depressed LA reservoir function leads to thromboembolic events is unclear. It is possible that the depressed LA reservoir function results in blood flow stasis in the LA and subsequent thrombus formation. Studies have also shown that low LA strains are associated with low flow velocities and thrombi in the LA appendage (LAA)[21], which is the most common site of intracardiac thrombus[22]. Of note, since none of the LV indices—mass, ejection fraction, EDV and longitudinal strain—were significantly associated with stroke/TIA, the role of the LA reservoir function in the pathogenesis of intracardiac thrombosis is not due to the indirect consequence of LV function. The possibility that cardioversion-induced atrial stunning could have confounded the findings is low because: (1) cardioversion was performed in only a minority of patients in both groups; (2) there was no significant difference in the fraction of patients who underwent cardioversion between both groups; and (3) CMR was performed approximately 8 weeks after cardioversion on average, while cardioversion-induced atrial stunning usually recovers within 4 weeks[23]. In the data set, there was no significant difference in the extent of the LA fibrosis quantified by LGE MRI between the stroke group and the control group. This finding is not consistent with a previous report[24], but this may be due to a small sample size since only a small number of patients underwent LGE (85 out of 169 patients).

LA Measurements by Tissue-Tracking CMR.

CMR has been established as a highly accurate and reproducible imaging modality, and is considered a standard clinical technique for measuring LA dimensions and volumes[25, 26]. LA volume and function was analyzed with tissue-tracking CMR, which has been used to measure multiple LA parameters with excellent intra- and inter-observer reproducibility in healthy subjects[10, 11]. Consistent with these previous reports, the results showed excellent inter- and intra-observer reproducibility for LA strain analysis with tissue-tracking CMR, which is similar or superior to those of speckle-tracking echocardiography[27] Additionally, tissue-tracking CMR can be performed with a routine cine CMR examination and does not require separate image acquisitions (e.g., tagged MRI or DENSE[28]) or contrast media, although contrast media might be used in clinical settings to identify LA wall fibrosis in LGE and LAA thrombus as a sign of possible impending stroke in CMR angiography before AF ablations[29]. Another strength of tissue-tracking CMR is that it is user-friendly. The images can be analyzed within minutes per patient by an operator without prior experience in image analysis, in contrast to LA fibrosis quantification with LGE that require hours of analysis per patient in the hands of an expert.

Clinical Implications.

The CHADS$_2$ and CHA$_2$DS$_2$-VASc scores are the most widely accepted and validated models to estimate the risk of stroke in AF patients[13, 14]. In addition, an increased LA volume is also associated with a higher risk of stroke[30]. Results described here demonstrate that the LA reservoir function is significantly associated with a prior history of stroke/TIA independent of the CHA$_2$DS$_2$-VASc score and the LA volume (Table 3). Results here offer a basis for determining the role of LA reservoir function by tissue-tracking CMR in predicting stroke or TIA. This may improve the current risk stratification strategy for stroke and potentially allow for early identification of subjects at risk of stroke, with or without a history of AF. Aggressive clinical management, such as early ablation or pharmacotherapy for AF to improve LA remodeling[31, 32] and early anticoagulation may reduce the risk of stroke in subjects with a high risk of stroke. In addition, further studies are warranted to investigate whether the risk of stroke improves if LA function improves by these therapies.

The reported study represents a single-center, retrospective, cross-sectional analysis. The analysis may be missing patients who died from stroke. In addition, CMR was not performed at the time of stroke/TIA. When evaluating the predictive value of the LA parameters for stroke, baseline LA strain analysis should ideally be assessed before stroke. For the deformation analysis, 2- and 4-chamber cine CMR was used, which was included in a routine image acquisition protocol. In certain embodiments, the strain was 2-D and was obtained in the in-plane direction. These strains can also be compared with 3-D strains. In addition, the endo- and epicardial contours included the ostium of pulmonary veins and the LAA in a small number of patients. This could have led to underestimation of strain values; however, two previous studies used the same approach and validated the results[10, 11]. Despite the limitations of certain methods used in certain embodiments of the invention, the analysis demonstrated a significant association between LA dysfunction and a prior history of stroke with excellent reproducibility (Table 4). Therefore, the advantage of certain embodiments of the instant invention outweigh the disadvantages of including more views (e.g., multiple short-axis LA slices) and of excluding the ostia area to assess the whole LA deformation, which would increase the scan time and post-processing burden.

Conclusions

CMR measurements indicate that lower LA total EF, $S_{max}$, and $SR_s$—representing LA reservoir function—are significantly associated with a prior history of stroke/TIA in patients with a history of AF. Our results offer a basis for a prospective study to determine the role of depressed LA reservoir function by tissue-tracking CMR in predicting stroke or TIA for early detection of the population at risk of developing stroke.

Materials and Methods

Study Design.

Figure 2:
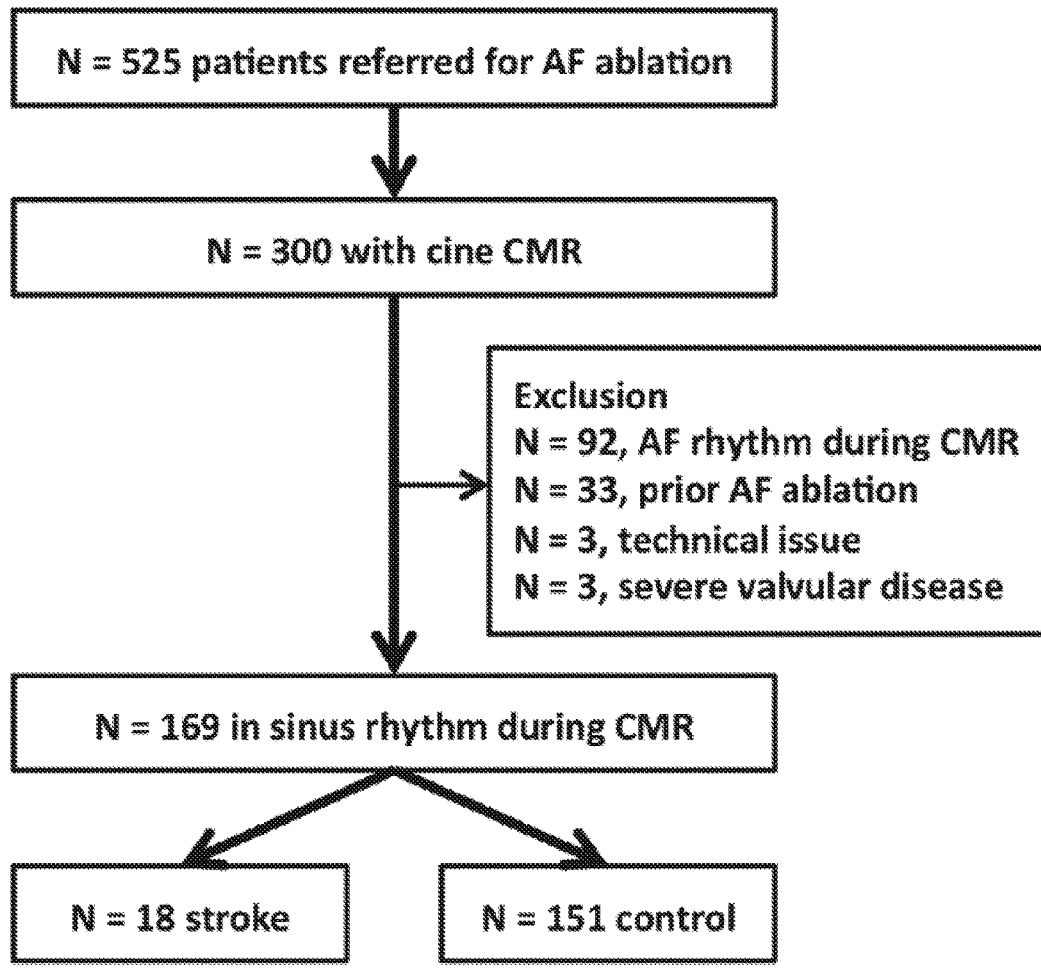
FIG. 2 is a schematic of patient enrollment.

To study the association between a prior history of stroke or TIA and LA structure and function as determined by tissue-tracking CMR, a single-center, retrospective, cross-sectional study was performed within a longitudinal, prospectively enrolled database for all the patients referred to the Johns Hopkins Hospital for catheter ablation of AF. Between June 2010 and August 2013, 525 consecutive patients were referred to the Johns Hopkins Hospital for AF ablation (FIG. 2). FIG. 2 is a schematic showing patient enrollment. In FIG. 2, AF=atrial fibrillation; CMR=cardiovascular magnetic resonance. Among these, 300 patients underwent a routine pre-ablation CMR. Patients who were in AF at the time of CMR (n=92, 31%) were excluded because the CMR image quality is often poor and the measured LA strains are depressed during AF compared with those in sinus rhythm[12]. Patients who had a prior AF ablation procedure (n=33), severe valvular disease in echocardiography (n=3), or poor-quality CMR images (n=3) were also excluded. Thus, 169 patients were included in the final analysis. The stroke group (n=18, 11.8%) was identified as those with a prior history of stroke or TIA at the time of CMR; the remaining patients were designated as the control group (n=151). The patients were classified as having either paroxysmal or persistent AF based on the guidelines[9], and the thromboembolic risk was assessed using the CHADS$_2$ and the CHA$_2$DS$_2$-VASc scores[13, 14]. In general, the patients with persistent AF were placed on antiarrhythmic medications and referred for external cardioversion 3-4 weeks prior to CMR[15]. All patients gave an informed consent to be included in the prospective patient database prior to the pre-ablation CMR, and the protocol was approved by the Institutional Review Board of the Johns Hopkins Medicine.

CMR Protocol.

CMR was performed with a 1.5 T scanner (Avanto; Siemens Medical Systems, Erlangen, Germany) and a 6-channel phased array body coil in combination with a 6-channel spine matrix coil. All images were electrocardiogram gated and acquired with breath-holding, with the patient in a supine position. Cine CMR images were scanned in the radial long axis by True Fast Imaging with Steady-State Precession (TrueFISP) sequence with a TE/TR and flip angle of 1.2/2.4 msec and 80 degrees, an in-plane resolution of 1.4×1.4 mm, a slice thickness of 8 mm, and a spacing of 2 mm. The images were acquired with 30 frames during the time interval between the R-peak of the ECG (temporal resolution, 20-40 ms). Among the 169 patients included in the final analysis, 85 (n=5 in the stroke group and n=80 in control group) also underwent late gadolinium enhancement (LGE) to quantify LA fibrosis. LGE-MRI scans were acquired within a range of 15-25 minutes after the injection of gadopentetate dimeglumine (0.2 mmol/kg, Bayer Healthcare Pharmaceuticals, Montville, N.J.) using a fat-saturated 3-dimensional (3-D) inversion recovery-prepared fast spoiled gradient-recalled echo sequence with the following: respiratory navigation and electrocardiogram gating with TE/TR and flip angle of 1.52/3.8 msec and 10°, an in-plane resolution of 1.3×1.3 mm, and a slice thickness of 2.0 mm. Trigger time for 3-D LGE-MRI images was optimized to acquire imaging data during diastole of LA as observed from the cine images. The optimal inversion time was identified with an inversion time scout scan (median 270 ms; range 240-290 ms) to maximize nulling of the LA myocardium. A parallel imaging technique—generalized autocalibrating partially parallel acquisition (reduction factor 2)—was used. Image processing was conducted in QMass MR (version 7.2, Leiden University Medical Center, Leiden, The Netherlands) on multiplanar reformatted axial images from 3-dimensional axial image data. To define LA fibrosis, the cutoff value of >0.97 for image intensity ratio (IIR) was used, which has been shown to correspond to the bipolar voltage<0.5 mV[16].

Tissue-Tracking CMR.

Figure 3A:
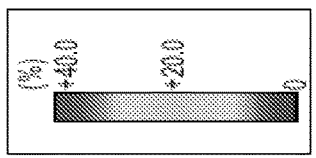
FIG. 3A-3E are images and graphs showing Left Atrium (LA) measurements by tissue-tracking Cardiac Magnetic resonance (CMR) in a patient without a stroke.
Figure 3A:
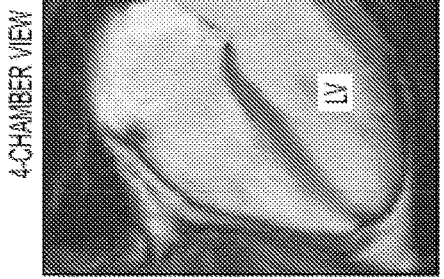
Figure 3B:
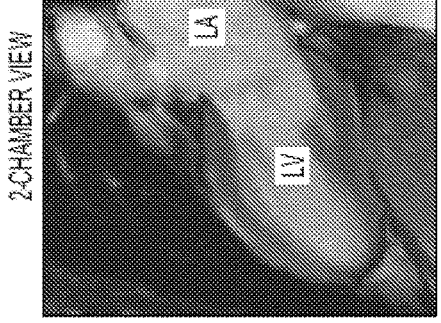

Off-line semi-automated multimodality tissue-tracking (MTT) software version 6.0 (Toshiba, Tokyo, Japan) was used to analyze the LA and LV structure and function in long-axis 2- and 4-chamber cine images[11]. The endo- and epicardial borders, excluding pulmonary veins and LA appendage, were manually traced. The number of pixels that lay across the LA and LV wall was 2.2±1.2 and 8.8±2.7, respectively. MTT is similar in concept to 2-dimensional (2-D) speckle-tracking imaging. Briefly, MTT reads characteristic pixel patterns in each 10 mm×10 mm area as template pieces from the reference image. The identified area as a template was searched in the next frame to find the best match according to the mean squared error of the image pixel intensity. This was used to accurately track pixel locations between subsequent image frames. Repeating the algorithm, the LA wall was automatically tracked through the cardiac cycle (FIGS. 3A, 3B). With this 2-D displacement field over time from the reference configuration to the deformed configuration, the differentiation with respect to the reference configuration gives the deformation gradient tensor (F), which depends on position. The Lagrangian Green's strain tensor (E) was then calculated as:

$$E = \frac{1}{2}(F^T F - I) \tag{1}$$

where $F^T$ is the transpose of F and I is the identity matrix. The strain (S) was defined as a stretch ratio along the longitudinal axis that represents the length normalized to its length at the reference configuration:

$$S = 100 \times \sqrt{2E_{ll}+1} \, (\%) \tag{2}$$

where $E_{ll}$ is the strain with respect to the local longitudinal axis calculated from the E.

The global longitudinal strain and strain rate were calculated by averaging all of the strain values obtained in long-axis 2- and 4-chamber views. A positive and negative strain value indicates stretch and shortening, respectively, with respect to the reference configuration at the ventricular end-diastole defined as the peak of R wave on surface ECG. LA maximum strain ($S_{max}$) and pre-atrial contraction strain ($S_{preA}$) were identified from the strain curve (FIG. 3D); the strain rates in LV systole ($SR_s$), LV early diastole ($SR_e$), and LA contraction ($SR_a$) were obtained from the strain rate curve (FIG. 3E).

FIGS. 3A-E shows images and graphs showing LA measurements by tissue-tracking CMR in a patient without a stroke. In FIGS. 3A and B, Left atrium (LA) longitudinal strain in the 2- and 4-chamber views at the end of left ventricular (LV) systole. (C) LA volume curve. The pink dotted line is the average of the values of volume in the 2- and 4-chamber views. The LA maximum volume ($V_{max}$), the pre-atrial contraction volume ($V_{preA}$), and the minimum volume ($V_{min}$) were identified. The LA emptying fractions (EFs) were calculated using $V_{max}$, $V_{preA}$, and $V_{min}$. (D and E) The LA strain and strain rate curve. The LA maximum strain ($S_{max}$) and pre-atrial contraction strain ($S_{preA}$) were identified from the strain curve. The strain rates during LV systole ($SR_s$), LV early diastole ($SR_e$), and atrial contraction ($SR_a$) were also analyzed from the strain rate curve.

Figure 3C:
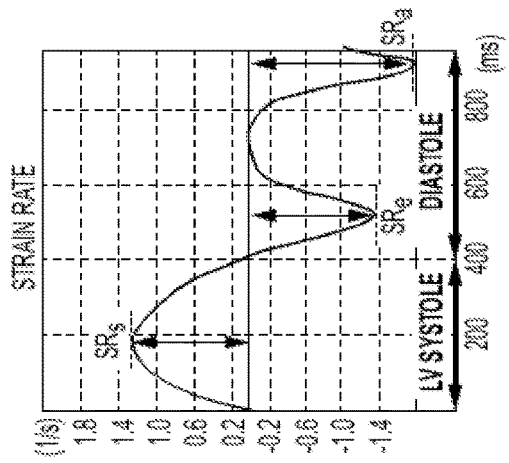
Figure 3D:
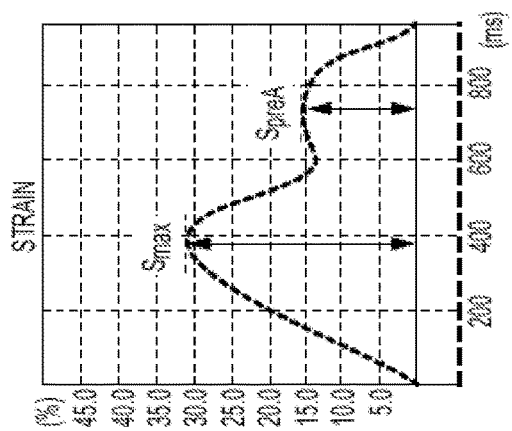
Figure 3E:
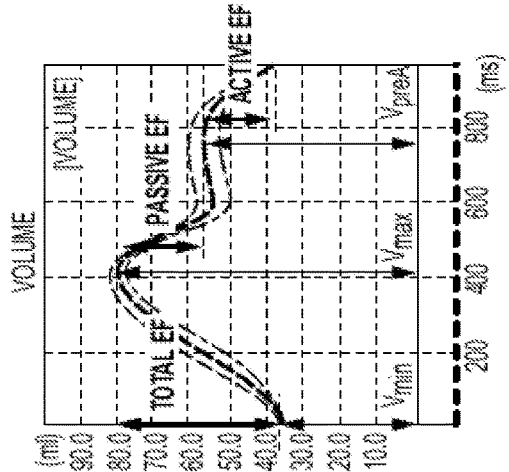

The LA volume curve was generated by the biplane modified Simpson's method, which was validated using the area-length method[17-19], and the maximum LA volume ($V_{max}$), pre-atrial contraction LA volume ($V_{preA}$), and minimum LA volume ($V_{min}$) were extracted (FIG. 3C). All the LA volumes were indexed by the body surface area (BSA) according to DuBois' formula (e.g., BSA=0.007184× [weight^0.425]×[height^0.725]). From the LA volumes, the LA emptying fractions (EF) were calculated as follows[20]: (1) LA total EF=($V_{max}$−$V_{min}$)×100%/$V_{max}$, (2) LA passive EF=($V_{max}$−$V_{preA}$)×100%/$V_{max}$, and (3) LA active EF= ($V_{preA}$−$V_{min}$)×100%/$V_{preA}$.

Reproducibility.

Intra- and inter-observer reproducibility for the LA parameters were examined in a group of 20 randomly selected patients by one investigator who made two independent measurements, and by two other investigators who were unaware of the other investigator's measurements and of the study time point. The bias (mean difference) and limits of agreement [1.96 standard deviation (SD) of difference] between the first and second measurements were determined by the Bland-Altman method. Intra-class correlation coefficients (ICC) were also assessed to evaluate reproducibility.

Statistical Analysis.

Continuous variables were presented as the means±SD and categorical variables as frequencies and percentages. The participants' baseline data and LA parameters were compared between the stroke and the control groups using Student's t-test for continuous variables and chi-square test for categorical variables. Univariable and multivariable logistic regression analyses were performed to evaluate the association between clinical variables and stroke/TIA. Model 1 reflected (univariable) unadjusted relations of LA and LV measurements to stroke/TIA. Model 2 was adjusted for the $CHA_2DS_2$-VASc score prior to stroke/TIA to incorporate a history of Cardiac failure, Hypertension, Age, Diabetes, Stroke/TIA, Vascular disease, and Sex. In Model 3, an additional adjustment was made for the LA $V_{min}$. The incremental value for assessing the risk of stroke was studied by calculating the improvement in the global chi-square. Data were analyzed with JMP version 10.0 (SAS Institute, Inc., Cary, N.C.) and MedCalc version 13.3 (MedCalc Software, Inc., Mariakerke, Belgium). A two-sided p-value of less than 0.05 was considered statistically significant.

REFERENCES FOR EXAMPLE 1

1. Mozaffarian D, Benjamin E J, Go A S, Arnett D K, Blaha M J, Cushman M, de Ferranti S, Despres J, Fullerton H J, Howard V J, Huffman M D, Judd S E, Kissela B M, Lackland D T, Lichtman J H, Lisabeth L D, Liu S, Mackey R H, Matchar D B, McGuire D K, Mohler E R, 3rd, Moy C S, Muntner P, Mussolino M E, Nasir K, Neumar R W, Nichol G, Palaniappan L, Pandey D K, Reeves M J, Rodriguez C J, Sorlie P D, Stein J, Towfighi A, Turan T N, Virani S S, Willey J Z, Woo D, Yeh R W, Turner M B. Heart Disease and Stroke Statistics-2015 Update: A Report From the American Heart Association. *Circulation.* 2014
2. Hart R G. Atrial fibrillation and stroke prevention. *N Engl J Med.* 2003; 349:1015-1016.
3. Benjamin E J, D'Agostino R B, Belanger A J, Wolf P A, Levy D. Left atrial size and the risk of stroke and death. The Framingham Heart Study. *Circulation.* 1995; 92:835-841.
4. Wong J M, Welles C C, Azarbal F, Whooley M A, Schiller N B, Turakhia M P. Relation of left atrial dysfunction to ischemic stroke in patients with coronary heart disease (from the heart and soul study). *Am J Cardiol.* 2014; 113:1679-1684.
5. Russo C, Jin Z, Liu R, Iwata S, Tugcu A, Yoshita M, Homma S, Elkind M S, Rundek T, Decarli C, Wright C B, Sacco R L, Di Tullio M R. LA volumes and reservoir function are associated with subclinical cerebrovascular disease: the CABL (Cardiovascular Abnormalities and Brain Lesions) study. *JACC Cardiovasc Imaging.* 2013; 6:313-323.
6. Habibi M, Lima J A, Khurram I M, Zimmerman S L, Zipunnikov V, Fukumoto K, Spragg D, Ashikaga H, Rickard J, Marine J E, Calkins H, Nazarian S. Association of left atrial function and left atrial enhancement in patients with atrial fibrillation: cardiac magnetic resonance study. *Circ Cardiovasc Imaging.* 2015; 8
7. Shih J Y, Tsai W C, Huang Y Y, Liu Y W, Lin C C, Huang Y S, Tsai L M, Lin L J. Association of decreased left atrial strain and strain rate with stroke in chronic atrial fibrillation. *J Am Soc Echocardiogr.* 2011; 24:513-519.
8. Obokata M, Negishi K, Kurosawa K, Tateno R, Tange S, Arai M, Amano M, Kurabayashi M. Left atrial strain provides incremental value for embolism risk stratification over CHA(2)DS(2)-VASc score and indicates prognostic impact in patients with atrial fibrillation. *J Am Soc Echocardiogr.* 2014; 27:709-716 e704.
9. January C T, Wann L S, Alpert J S, Calkins H, Cigarroa J E, Cleveland J C, Jr., Conti J B, Ellinor P T, Ezekowitz M D, Field M E, Murray K T, Sacco R L, Stevenson W G, Tchou P J, Tracy C M, Yancy C W. 2014 AHA/ACC/HRS Guideline for the Management of Patients With Atrial Fibrillation: A Report of the American College of Cardiology/American Heart Association Task Force on Practice Guidelines and the Heart Rhythm Society. *Circulation.* 2014; 130:e199-267.
10. Habibi M, Chahal H, Opdahl A, Gjesdal O, Helle-Valle T M, Heckbert S R, McClelland R, Wu C, Shea S, Hundley G, Bluemke D A, Lima J A. Association of CMR-measured LA function with heart failure development: results from the MESA study. *JACC Cardiovasc Imaging.* 2014; 7:570-579.
11. Imai M, Ambale Venkatesh B, Samiei S, Donekal S, Habibi M, Armstrong A C, Heckbert S R, Wu C O, Bluemke D A, Lima J A. Multi-ethnic study of atherosclerosis: association between left atrial function using tissue tracking from cine MR imaging and myocardial fibrosis. *Radiology.* 2014; 273:703-713.
12. Inaba Y, Yuda S, Kobayashi N, Hashimoto A, Uno K, Nakata T, Tsuchihashi K, Miura T, Ura N, Shimamoto K. Strain rate imaging for noninvasive functional quantification of the left atrium: comparative studies in controls and patients with atrial fibrillation. *J Am Soc Echocardiogr.* 2005; 18:729-736.
13. Gage B F, Waterman A D, Shannon W, Boechler M, Rich M W, Radford M J. Validation of clinical classification schemes for predicting stroke. *JAMA.* 2001; 285:2864-2870.
14. Lip G Y, Nieuwlaat R, Pisters R, Lane D A, Crijns H J. Refining clinical risk stratification for predicting stroke and thromboembolism in atrial fibrillation using a novel risk factor-based approach. *Chest.* 2010; 137:263-272.
15. Rivard L, Hocini M, Rostock T, Cauchemez B, Forclaz A, Jadidi A S, Linton N, Nault I, Miyazaki S, Liu X, Xhaet O, Shah A, Sacher F, Derval N, Jais P, Khairy P, Made L, Nattel S, Willems S, Haissaguerre M. Improved outcome following restoration of sinus rhythm prior to catheter ablation of persistent atrial fibrillation: a comparative multicenter study. *Heart Rhythm.* 2012; 9:1025-1030.
16. Khurram I M, Beinart R, Zipunnikov V, Dewire J, Yarmohammadi H, Sasaki T, Spragg D D, Marine J E, Berger R D, Halperin H R, Calkins H, Zimmerman S L, Nazarian S. Magnetic resonance image intensity ratio, a normalized measure to enable interpatient comparability of left atrial fibrosis. *Heart Rhythm.* 2014; 11:85-92.
17. Ujino K, Barnes M E, Cha S S, Langins A P, Bailey K R, Seward J B, Tsang T S. Two-dimensional echocardiographic methods for assessment of left atrial volume. *Am J Cardiol.* 2006; 98:1185-1188.
18. Habibi M, Chahal H, Opdahl A, Gjesdal O, Helle-Valle T M, Heckbert S R, McClelland R, Wu C, Shea S, Hundley G, Bluemke D A, Lima J A C. Association of CMR-measured LA function with heart failure development: results from the MESA study. *JACC Cardiovasc Imaging.* 2014; 7:570-579.
19. Nacif M S, Barranhas A D, Turkbey E, Marchiori E, Kawel N, Mello R A, Falcao R O, Oliveira A C, Jr., Rochitte C E. Left atrial volume quantification using cardiac MRI in atrial fibrillation: comparison of the Simpson's method with biplane area-length, ellipse, and three-dimensional methods. *Diagn Interv Radiol.* 2013; 19:213-220.
20. Farzaneh-Far A, Ariyarajah V, Shenoy C, Dorval J F, Kaminski M, Curillova Z, Wu H, Brown K B, Kwong R Y. Left atrial passive emptying function during dobutamine stress MR imaging is a predictor of cardiac events in patients with suspected myocardial ischemia. *JACC Cardiovasc Imaging.* 2011; 4:378-388.
21. Karabay C Y, Zehir R, Guler A, Oduncu V, Kalayci A, Aung S M, Karagoz A, Tanboga I H, Candan O, Gecmen C, Erkol A, Esen A M, Kirma C. Left atrial deformation parameters predict left atrial appendage function and thrombus in patients in sinus rhythm with suspected cardioembolic stroke. *Echocardiography.* 2013; 30:572-581.
22. Stoddard M F, Dawkins P R, Prince C R, Ammash N M. Left atrial appendage thrombus is not uncommon in patients with acute atrial fibrillation and a recent embolic event: a transesophageal echocardiographic study. *J Am Coll Cardiol.* 1995; 25:452-459.
23. Khan I A. Transient atrial mechanical dysfunction (stunning) after cardioversion of atrial fibrillation and flutter. *Am Heart J.* 2002; 144:11-22.
24. Daccarett M, Badger T J, Akoum N, Burgon N S, Mahnkopf C, Vergara G, Kholmovski E, McGann C J, Parker D, Brachmann J, MacLeod R S, Marrouche N F. Association of left atrial fibrosis detected by delayed-enhancement magnetic resonance imaging and the risk of stroke in patients with atrial fibrillation. *J Am Coll Cardiol.* 2011; 57:831-838.
25. Maceira A M, Cosin-Sales J, Roughton M, Prasad S K, Pennell D J. Reference left atrial dimensions and volumes by steady state free precession cardiovascular magnetic resonance. *J Cardiovasc Magn Reson.* 2010; 12:65.
26. Hof I E, Velthuis B K, Van Driel V J, Wittkampf F H, Hauer R N, Loh P. Left atrial volume and function assessment by magnetic resonance imaging. *J Cardiovasc Electrophysiol.* 2010; 21:1247-1250.
27. Motoki H, Dahiya A, Bhargava M, Wazni O M, Saliba W I, Marwick T H, Klein A L. Assessment of left atrial mechanics in patients with atrial fibrillation: comparison between two-dimensional speckle-based strain and velocity vector imaging. *J Am Soc Echocardiogr.* 2012; 25:428-435.
28. Schmidt E J, Fung M M, Ciris P A, Song T, Shankaranarayanan A, Holmvang G, Gupta S N, Chaput M, Levine R A, Ruskin J, Reddy V Y, D'Avila A, Aletras A H, Danik S B. Navigated DENSE strain imaging for post-radiofrequency ablation lesion assessment in the swine left atria. *Europace.* 2014; 16:133-141.
29. Rathi V K, Reddy S T, Anreddy S, Belden W, Yamrozik J A, Williams R B, Doyle M, Thompson D V, Biederman R W W. Contrast-enhanced CMR is equally effective as TEE in the evaluation of left atrial appendage thrombus in patients with atrial fibrillation undergoing pulmonary vein isolation procedure. *Heart Rhythm.* 2013; 10:1021-1027.
30. Osranek M, Bursi F, Bailey K R, Grossardt B R, Brown R D, Jr., Kopecky S L, Tsang T S, Seward J B. Left atrial volume predicts cardiovascular events in patients originally diagnosed with lone atrial fibrillation: three-decade follow-up. *Eur Heart J.* 2005; 26:2556-2561.
31. Tsang T S M, Barnes M E, Abhayaratna W P, Cha S S, Gersh B J, Langins A P, Green T D, Bailey K R, Miyasaka Y, Seward J B. Effects of quinapril on left atrial structural remodeling and arterial stiffness. *Am J Cardiol.* 2006; 97:916-920.
32. Perea R J, Tamborero D, Mont L, De Caralt T M, Ortiz J T, Berruezo A, Matiello M, Sitges M, Vidal B, Sanchez M, Brugada J. Left atrial contractility is preserved after successful circumferential pulmonary vein ablation in patients with atrial fibrillation. *J Cardiovasc Electrophysiol.* 2008; 19:374-379.

Example 2: Personalized Left Atrial Blood Flow Analysis Using Computational Fluid Dynamics This study presents a computational framework to perform CT-based, personalized blood flow analysis in human left atrium (LA). Patient-specific LA geometry and function were obtained from the cardiac CT images of a patient acquired during sinus rhythm. A four-dimensional displacement vector field was estimated using a non-rigid registration method. The LA blood outflow across the mitral valve was calculated from LV volume change, and the flow field within the LA was derived from computational fluid dynamics (CFD) using the incompressible Navier-Stokes equation. The global characteristiscs of the LA motion and blood flow excellently agreed with clinical observations. The personalized blood flow analysis in the LA may be useful to evaluate the flow stasis associated with the risk of the intracardiac thrombosis and stroke.

Key Words: Atrial Fibrillation, Computational Fluid Dynamics, Cardiac Mechanics, Left Atrium 1. Introduction Atrial fibrillation (AF) is associated with an increased risk of stroke[1]. However, recent studies suggest that AF may not be mechanistically responsible for the thromboembolic events[2-4] and instead indicate that alterations in cardiac structure and function that serve as an arrhythmic substrate for AF may be causally related to thromboembolism. For example, indices of left atrial (LA) structural remodelling, including larger LA size[5], larger extent of LA fibrosis[6], lower LA functions[7], and lower LA appendage (LAA) function[8] in sinus rhythm are known markers of stroke.

Computational fluid dynamics (CFD) is thought to be a beneficial tool to link all markers of structural remodelling and blood flow characteristics in the LA attributed the thromboembolic events. However, in earlier studies[9,10], LA function was treated by an ideal condition rather than measured in individual patients. Since the LA function is one of the critical determinant of blood flow within the LA, patient-specific LA function quantified by 3D high-resolution imaging would improve the accuracy of personalized blood flow analysis in individual patients.

The present study presents a computational framework to conduct personalized blood flow analysis in the LA. We used a motion-estimation CT to acquire patient-specific LA geometry and function.

Figure 6A:
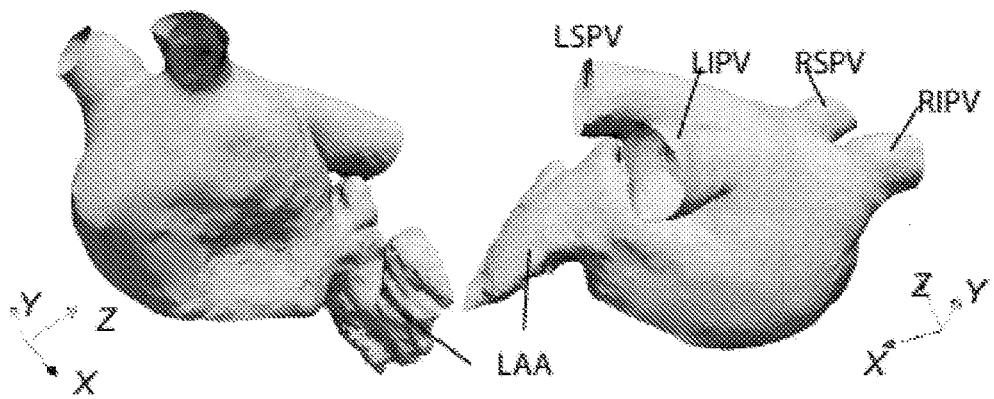
FIG. 6A is a model showing the geometry of left atrium (LA) and the left atrial appendage (LAA) on anterior view (left) and posterior view (right). Left superior and inferior pulmonary arteries (LSPV and LIPV) and right superior and inferior arteries (RSPV and RIPV) are also shown.
Figure 6B:
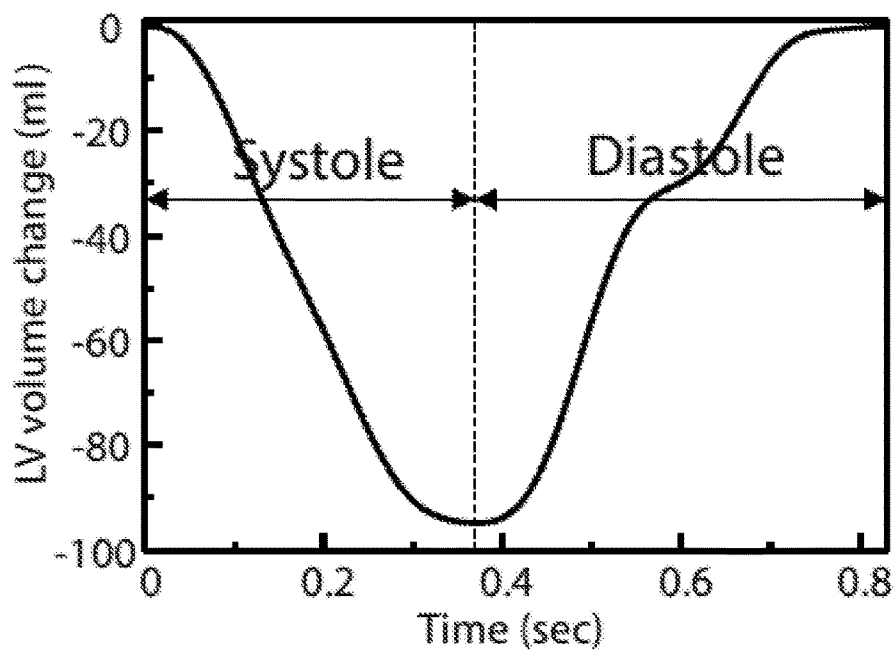
FIG. 6B is a graph showing a time course of left ventricular volume change during the cardiac cycle.

2. Computational Methods 2.1 Acquisition of a Patient-Specific LA Geometry and Function In this study, we used cardiac CT images of an AF patient acquired during normal sinus rhythm using a 64-slice multi-detector CT scanner (Aquilion 64, Toshiba America Medical Systems, Inc. Tustin, Calif.). The volumetric CT images were reconstructed for a total of 20 phases during one cycle length. The reconstructed image matrix size was 512×512×298 with the voxel size of 0.5×0.5×0.5 $mm^3$. LA was segmented in the CT images at all the 20 phases using the cardiovascular segmentation tool of Mimics Medical 18.0 (Materialise, Inc. Plymouth, Mich.). Using the segmented CT images, LA surface geometry reconstruction and LV volume measurements were performed at all the phases. FIGS. 6A and 6B show representative LA surface geometry and time course of LV volume changes. The cycle length of the cardiac cycle was 0.82 sec.

Motion estimation of the LA wall was performed by a non-rigid registration method developed by Pourmorteza et al[11]. The template point set was constructed from the LA surface mesh at electrocardiographic ventricular end diastole using Pointwise V17.3R1 (Pointwise, Inc. Fort Worth, Tex.) with the base mesh size of 1.5 mm. From the matched point sets in all phases, three-dimensional displacement vectors of all points were calculated. These discrete displacement vectors given in 20 phases were interpolated to the continuous function given in arbitrary time t expressed by using the methods of Chnafa et al[12].

Patient-specific volumes of blood ejected through the MV from LA to LV over time were calculated from the changes in LV volumes during ventricular diastole. To minimize the computational cost, the LV was modelled as a cylinder that receives the patient-specific blood volume during ventricular diastole. The MV was considered to be closed during ventricular systole and open during ventricular diastole, and the time required for MV opening and closure was considered to be negligible. Ventricular systole and diastole were defined by the time course of LV volume.

2.2 Left Atrial Blood Flow Analysis

Tetrahedral meshes were constructed in the LA including the PVs using Pointwise for the blood flow analysis. Blood flow analysis in the LA was implemented in Open-FOAM 2.3.1 (http://www.openfoam.com/). We assumed the blood as an incompressible Newtonian fluid with density $\rho$ of $1.05 \times 10^3$ kg/m$^3$ and viscosity $\mu$ of $3.5 \times 10^{-3}$ Pa·s. The flow in the LA was modelled with the incompressible Navier-Stokes equation and the equation of continuity. These equations were solved with coupling using the Pressure Implicit with Splitting of Operations (PISO) algorism.

For the boundary conditions of the CFD studies, the velocity at the wall boundary was determined by the wall motion in each time step and the zero gradient pressure was adopted. At the distal end of each PV, the velocity was determined by the flow direction: zero-gradient velocity for outflow and a fixed velocity calculated from the flux through the boundary for inflow using a routine in Open-FOAM. This boundary condition was chosen to permit both inflow and outflow in the PVs that are observed during the cardiac cycle in human heart[13]. The pressure is set to satisfy the total pressure to be zero. The boundary condition of the MV annulus during ventricular systole was treated as a wall boundary.

For the volume mesh deformation, displacement vector calculated by the motion estimation was assigned in the nodes of the whole wall boundary, except the distal end of the PVs and the MV annulus during ventricular systole which were set to a zero-gradient boundary. The blood flow analysis in each case was performed with the time increment of $1 \times 10^{-4}$ sec. A total of 5 cardiac cycles were calculated in each case. In the preliminary calculation, we confirmed that flow characteristics reached a stable condition and became periodic within the first three cardiac phases.

3. Results and Discussion 3.1 Time Course of LA and LAA Volume Change

Figure 7:
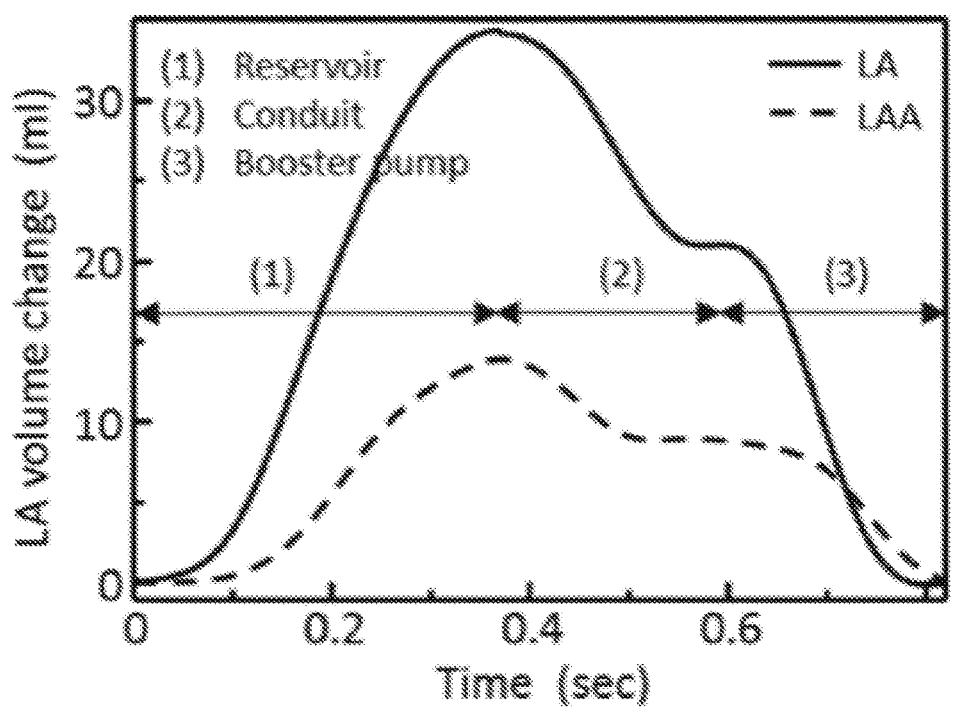
FIG. 7 is a chart showing a time course of volume change of left atrium (LA) and left atrial appendage (LAA) during the cardiac cycle.

The time course of LA and LAA volume change with reference to the ventricular end-diastole was calculated from motion estimation results shown in FIG. 7. The time course clearly showed three characteristic phases of LA function: the reservoir phase for pulmonary venous return during LV systole, the conduit phase for pulmonary venous return during LV early diastole, and the booster pump phase that augments LV filling during LV late diastole. The LA and the LAA accounted for approximately 60% of LV filling volume, which is consistent with our previous data using cardiac MRI[7].

3.2 LA Global Flow Characteristics

Figure 8:
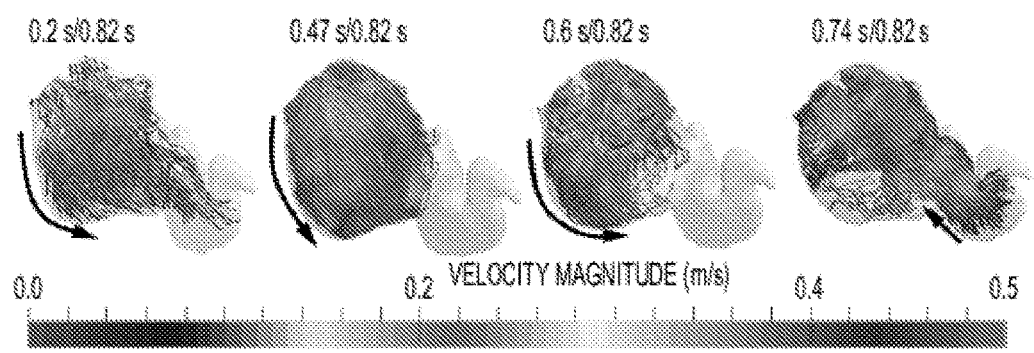
FIG. 8 is a model showing the streamlines of blood flow in a representative cardiac cycle in the anterior view of the LA.

FIG. 8 shows the streamlines of blood flow in a representative cardiac cycle in the anterior view of the LA. The blood flow from the all pulmonary veins (PVs) swirled counterclockwise along the top of the LA and the septum during the reservoir phase [FIG. 8 (0.2 sec)]. During the conduit phase, this swirling flow was replaced by longitudinal flow of high velocity magnitude coming from all PVs to pass through the MV [FIG. 8 (0.47 sec)]. At the end of the conduit phase, the longitudinal flow was replaced transiently by the swirling flow [FIG. 8 (0.6 sec)]. During the booster pump phase the swirling flow immediately disappeared, followed by appearance of outflow (flow coming out of LA) in all PVs [FIG. 8 (0.74 sec)]. These time course of LA global flow characteristics was consistent with that of the healthy human LA reported in Fyrenius et al.[14]. In addition, we confirmed the time course of the velocity magnitude in the LAA showed also excellent agreement between CFD results and measurement results by using the transesophageal echocardiography (not shown). Therefore, we believe that our computational framework of the personalized blood flow analysis can be used to evaluate the global features of the flow field in the LA in individual patients.

4. Summary

In the present study, we developed a computational framework to perform CT-based, personalized blood flow analysis in the LA. We confirmed the robustness of this framework through the correspondence between the CFD results and clinical observations. For the risk assessment of the thrombosis in the LA attributing the stroke, further analysis using large population dataset including the AF patients with and without the prior history of stroke is needed.

REFERENCES FOR EXAMPLE 2

1. Wolf P A, Abbott R D, Kannel W B. Original Contributions Atrial Fibrillation as an Independent Risk Factor for Stroke: The Framingham Study. *Stroke*. 1991: 983-988. doi:10.1161/01.STR.22.8.983.
2. Brambatti M, Connolly S J, Gold M R, et al. Temporal relationship between subclinical atrial fibrillation and embolic events. *Circulation*. 2014; 129(21):2094-2099. doi:10.1161/CIRCULATIONAHA.113.007825.
3. Daoud E G, Glotzer T V., Wyse D G, et al. Temporal relationship of atrial tachyarrhythmias, cerebrovascular events, and systemic emboli based on stored device data: A subgroup analysis of TRENDS. *Hear Rhythm*. 2011; 8(9):1416-1423. doi:10.1016/j.hrthm.2011.04.022.
4. Habibi M, Lima J A. C, Khurram I M, et al. Association of Left Atrial Function and Left Atrial Enhancement in Patients With Atrial Fibrillation: Cardiac Magnetic Resonance Study. *Circ Cardiovasc Imaging*. 2015; 8(2): e002769-e002769. doi:10.1161/CIRCIMAGING.114.002769.
5. Benjamin E J, D'Agostino R B, Belanger A J, Wolf P A, Levy D. Left Atrial Size and the Risk of Stroke and Death: The Framingham Heart Study. *Circulation*. 1995; 92(4): 835-841. doi:10.1161/01.CIR.92.4.835.
6. Daccarett M, Badger T J, Akoum N, et al. Association of left atrial fibrosis detected by delayed-enhancement magnetic resonance imaging and the risk of stroke in patients with atrial fibrillation. *J Am Coll Cardiol*. 2011; 57(7): 831-838. doi:10.1016/j.jacc.2010.09.049.
7. Inoue Y Y, Alissa A., Khurram I M, et al. Quantitative Tissue-Tracking Cardiac Magnetic Resonance (CMR) of Left Atrial Deformation and the Risk of Stroke in Patients with Atrial Fibrillation. *J Am Heart Assoc*. 2015; 4(4): e001844-e001844. doi:10.1161/JAHA.115.001844.
8. Al-Issa A, Inoue Y, Cammin J, et al. Regional function analysis of left atrial appendage using motion estimation CT and risk of stroke in patients with atrial fibrillation. *Eur Hear J—Cardiovasc Imaging*. 2015: jev207. doi: 10.1093/ehjci/jev207.
9. Zhang L, Gay M. Characterizing left atrial appendage functions in sinus rhythm and atrial fibrillation using computational models. *J Biomech.* 2008; 41(11):2515-23. doi:10.1016/j.jbiomech.2008.05.012.
10. Koizumi R, Funamoto K, Hayase T, et al. Numerical analysis of hemodynamic changes in the left atrium due to atrial fibrillation. *J Biomech.* 2015; 48(3):472-478. doi: 10.1016/j.jbiomech.2014.12.025.
11. Pourmorteza A, Schuleri K H, Herzka D a, Lardo A C, McVeigh E R. A new method for cardiac computed tomography regional function assessment: stretch quantifier for endocardial engraved zones (SQUEEZ). *Circ Cardiovasc Imaging.* 2012; 5(2):243-50. doi:10.1161/CIRCIMAGING.111.970061.
12. Chnafa C, Mendez S, Nicoud F. Image-based large-eddy simulation in a realistic left heart. *Comput Fluids.* 2014; 94:173-187. doi:10.1016/j.compfluid.2014.01.030.
13. Smiseth O A, Thompson C R, Lohavanichbutr K, et al. The pulmonary venous systolic flow pulse—its origin and relationship to left atrial pressure. *J Am Coll Cardiol.* 1999; 34(3):802-809. doi:10.1016/S0735-1097(99)00300-9.
14. Fyrenius A, Wigström L, Ebbers T, Karlsson M, Engvall J, Bolger A F. Three dimensional flow in the human left atrium. *Heart.* 2001; 86(4):448-455. doi:10.1136/heart.86.4.448.

Example 3: A Computational Framework for Personalized Blood Flow Analysis in the Human Left Atrium Abstract Atrial fibrillation (AF), the most common human arrhythmia, is a marker of an increased risk of embolic stroke. However, recent studies suggest that AF may not be mechanistically responsible for the stroke events. An alternative explanation for the mechanism of intracardiac thrombosis and stroke in patients with AF is structural remodeling of the left atrium (LA). However, a mechanistic link between LA structural remodeling and intracardiac thrombosis is unclear, because there is no clinically feasible methodology to evaluate the complex relationship between these two phenomena in individual patients. Computational fluid dynamics (CFD) is a powerful tool that could potentially link LA structural remodeling and intracardiac thrombosis in individual patients by evaluating the patient-specific LA blood flow characteristics. However, the lack of knowledge of the material and mechanical properties of the heart wall in specific patients makes it challenging to solve the complexity of fluid-structure interaction. In this study, our aim was to develop a clinically feasible methodology to perform personalized blood flow analysis within the heart. We propose an alternative computational approach to perform personalized blood flow analysis by providing the three-dimensional LA endocardial surface motion estimated from patient-specific cardiac CT images. In two patients (case 1 and 2), a four-dimensional displacement vector field was estimated using nonrigid registration. The LA blood outflow across the mitral valve (MV) was calculated from the LV volume, and the flow field within the LA was derived from the incompressible Navier-Stokes equation. The CFD results successfully captured characteristic features of LA blood flow observed clinically by transesophageal echocardiogram. The LA global flow characteristics and vortex structures also agreed well with previous reports. The time course of LAA emptying was similar in both cases, despite the substantial difference in the LA structure and function. We conclude that our CT-based, personalized LA blood flow analysis is a clinically feasible methodology that can be used to improve our understanding of the mechanism of intracardiac thrombosis and stroke in individual patients with LA structural remodeling.

List of Abbreviations: AF=Atrial fibrillation; CFD=Computational fluid dynamics; CT=Computed tomography; LA=Left atrium; LAA=Left atrial appendage; LV=Left ventricle; MV=Mitral valve; PV=Pulmonary vein; TEE=Transesophageal echocardiogram; 3-D=Three-dimensional; 4-D=Four-dimensional Introduction Atrial fibrillation (AF) is associated with an increased risk of embolic stroke[33]. However, recent studies using extended electrocardiographic monitoring revealed that most patients with acute stroke had no evidence of AF within one month prior to the event[6,9]. In addition, even a single six-minute episode of atrial arrhythmia is associated with a greater than two-fold risk of ischemic stroke[13]. These findings strongly suggest that AF may be a marker of an elevated thromboembolic risk, but may not be mechanistically responsible for the events[24]. Instead, alterations in cardiac structure and function that serve as an arrhythmic substrate for AF may be causally related to thromboembolism. In fact, indices of left atrial (LA) structural remodeling, including larger LA size[3,10,18,31], larger extent of LA fibrosis[8], lower LA function[14,26,34], and lower LA appendage (LAA) function[2,23] are known markers of stroke. However, a mechanistic link between LA structural remodeling and intracardiac thrombosis is unclear, because there is no clinically feasible methodology to evaluate the complex relationship between these two phenomena in individual patients.

Computational fluid dynamics (CFD) is a powerful tool that can provide a methodology to link LA structural remodeling and intracardiac thrombosis in individual patients by evaluating the patient-specific LA blood flow characteristics[19,35]. However, one of the challenges of personalized CFD analysis within the heart is the complexity of fluid-structure interaction between the blood flow and the heart wall, mainly resulting from the lack of knowledge of the material and mechanical properties of the heart wall in specific patients. In this study, our aim was to develop a clinically feasible methodology to perform personalized blood flow analysis within the heart. We propose an alternative approach to perform personalized blood flow analysis by providing the three-dimensional (3-D) LA endocardial surface motion estimated from patient-specific cardiac CT images. In essence, our approach reduces the cardiac CFD analysis to a moving boundary problem, which is clinically tractable in individual patients. The effectiveness of our approach is demonstrated by numerical examples of two human patients.

Materials and Methods

Figure 9:
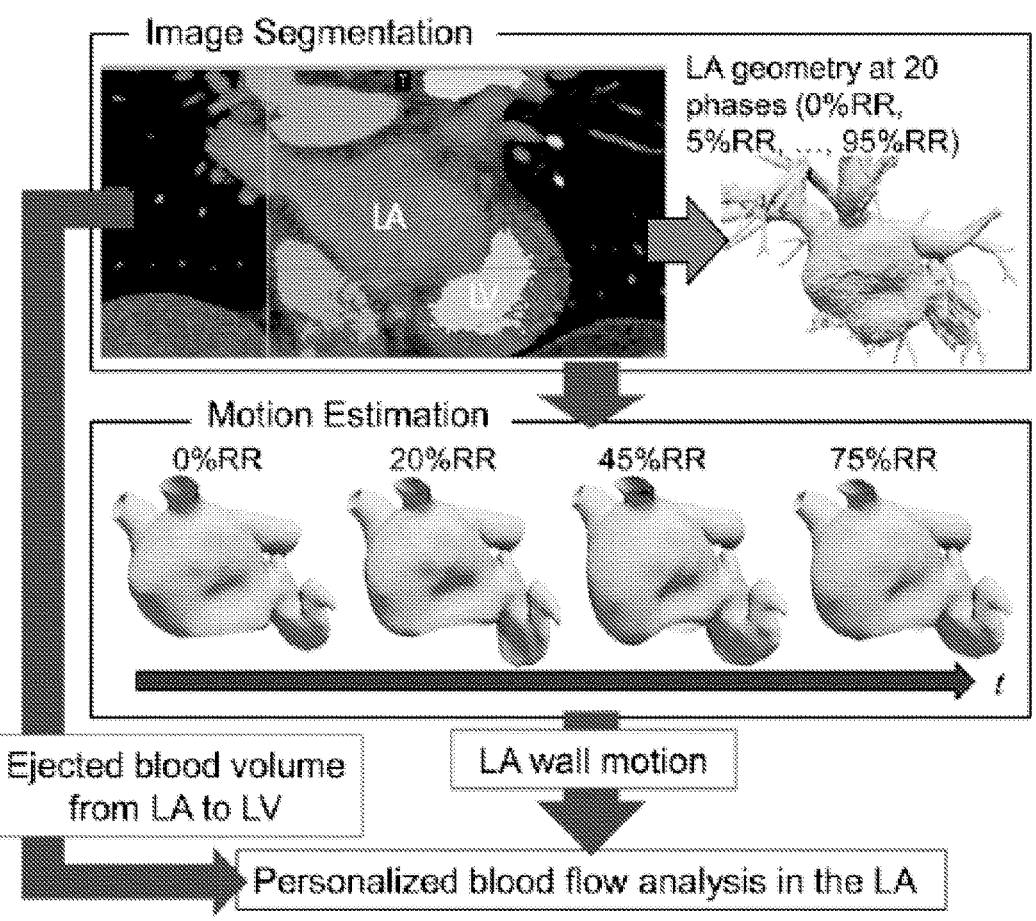
FIG. 9 is a schematic of workflow of personalized blood flow analysis in the left atrium.

The workflow of the LA personalized blood flow analysis is shown in FIG. 9. The protocol was approved by the Institutional Review Board of the Johns Hopkins Medicine. In FIG. 9, The CT images were segmented to reconstruct the left atrial (LA) surface structure and measure the left ventricular (LV) volume for a total of 20 phases in a cardiac cycle (0% RR, 5% RR, . . . , 95% RR), where the RR indicates the cycle length. Motion Estimation. The LA wall motion was estimated by a nonrigid registration method[25]. Personalized blood flow analysis in the LA was performed with patient-specific LA wall motion and ejected blood volume from LA to LV calculated by the LV volume change.

Patient-Specific Cardiac Structure.

Figure 10A:
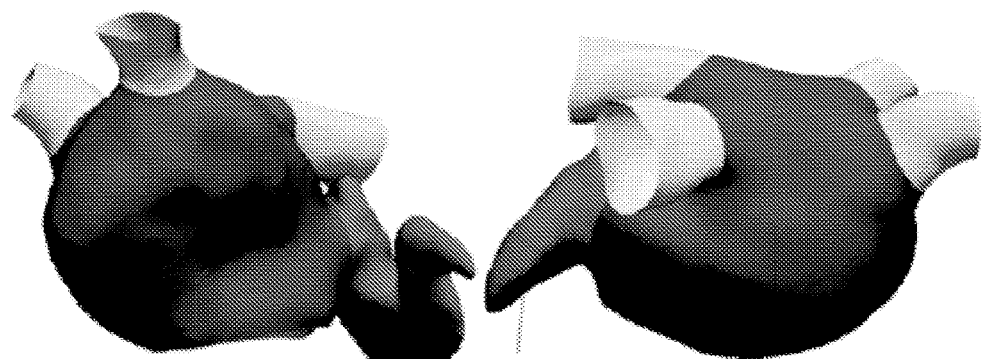
FIGS. 10A and 10B are schematics of Patient-specific left atrial geometry. The geometry of the left atrium (LA) and the left atrial appendage (LAA) represents 0% RR in both case 1 (FIG. 10A, top row) and case 2 (FIG. 10B, bot-tom row). The X, Y and Z axes indicate the coronal, axial, sagittal axes, respectively.
Figure 10B:
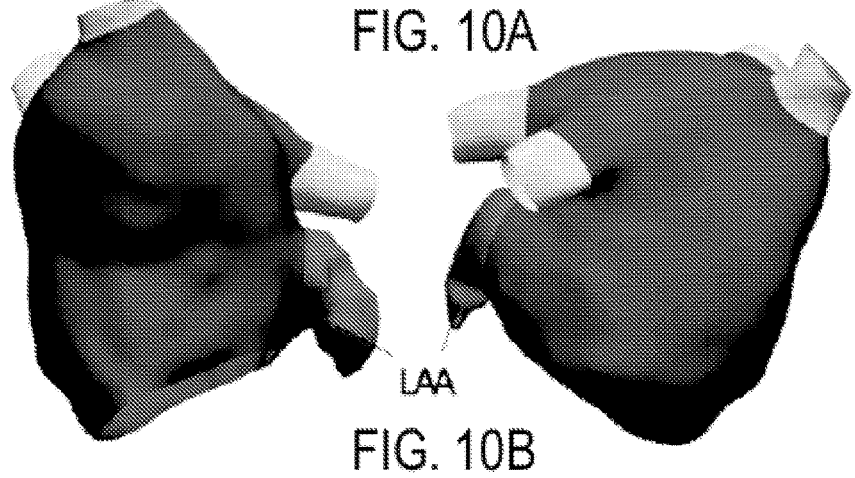

In this study we used cardiac CT images of two patients with a history of AF (case 1 and case 2) but without a prior history of stroke or transient ischemic attack. We acquired the CT images during normal sinus rhythm prior to catheter ablation of AF using a 64-slice multi-detector CT scanner (Aquilion 64, Toshiba America Medical Systems, Inc. Tustin, Calif.). We reconstructed the volumetric CT images for a total of 20 phases (0% RR, 5% RR, . . . , 95% RR) during the cardiac cycle. Here, the RR indicates the cycle length, or the interval between two consecutive electrocardiographic R waves, and 0% RR indicates electrocardiographic ventricular end-diastole. The reconstructed image matrix size was 512×512×298 for case 1 and 512×512×352 for case 2. The in-plane pixel size was 0.5×0.5 mm$^2$, the through-plane slice thickness was 1.0 mm, and slice gap was 0.5 mm, resulting in a 3-D image matrix of 0.5×0.5×0.5 mm$^3$. We segmented the endocardial surface of the LA and the left ventricle (LV) at all the phases on the basis of signal intensity using the cardiovascular segmentation tool of Mimics Medical 18.0 (Materialise, Inc. Plymouth, Mich.). We removed the pulmonary veins (PVs) beyond the first bifurcation using MeshMixer (Version 1.09.293; Autodesk, Inc. San Rafael, Calif.). We defined the triangular LA endocardial surface geometry at the reference phase (0% RR) as the template mesh using Pointwise (Version V17.3R1; Pointwise, Inc. Fort Worth, Tex.) with the base element size of 1.5 mm. This base element size was determined from the spatial resolution of the CT image (slice thickness of 1 mm) and a measurement error of one in-plane pixel size (=0.5 mm). The LA structure of both the cases is shown in FIGS. 10A and 10B. Of note, case 1 also underwent transesophageal echocardiogram (TEE) with Doppler-based blood velocity measurements within the LA under general anesthesia at a separate time point. The blood velocity data from TEE was used to validate our CFD results.

Patient-Specific Cardiac Function.

We used a nonrigid registration method developed by Pourmorteza et al.[25] to estimate the cardiac motion, which directly computes the 3-D displacement fields between the target mesh in the reference phase and a target mesh in all the other (deformed) phases such that every triangle on the template mesh has a corresponding triangle on each of the target mesh. To obtain the four-dimensional (4-D) continuous displacement field u(t) of the endocardial LA surface, we interpolated the discrete displacement fields $\bar{u}_i$ given in 20 phases (i=1, 2, . . . , 20) using inverse Fourier series expansion[7].

$$u(t) = \sum_{k=0}^{L} F_k \exp\left(\frac{2\pi i k t}{T}\right), \quad (1)$$

where T is the cycle length, L is the maximum Fourier mode, and $F_k$ is the Fourier coefficient, obtained from the Fourier transform of $\bar{u}_i$, which is the magnitude at frequency k/T. Since our CT system required approximately 0.15 seconds to reconstruct the cardiac images in each phase using the half-scan reconstruction method[21], we removed $F_k$ in the high frequency domain (>1/0.15≈6.7 sec$^{-1}$) which likely contained measurement errors.

Patient-Specific Left Atrial Blood Flow Analysis.

For the blood flow analysis, we created tetrahedral volumetric meshes in the LA at the reference phase using Pointwise. With the base element size of 1.5 mm, the total number of volumetric elements was 366,909 and 549,299 in case 1 and 2, respectively. We conducted a mesh convergence study to confirm that the volumetric element size did not substantially influence the solutions (see Appendix S1, Electronic Supplementary Material). We performed the LA blood flow analysis using OpenFOAM 2.3.1 (http://www.openfoam.com/). We assumed the blood to be an incompressible Newtonian fluid with density ρ of 1.05×10$^3$ kg/m$^3$ and viscosity μ of 3.5×10$^{-3}$ Pa·s, because the non-Newtonian effects on the global blood flow characteristics in large domains such as the LA are considered to be negligible[20]. The flow in the LA was modeled with the incompressible Navier-Stokes equation and the continuity equation, given by $$\frac{\partial v}{\partial t} + v \cdot \nabla v = -\frac{1}{\rho}\nabla p + \frac{\mu}{\rho}\nabla^2 v, \quad (1)$$

$$\nabla \cdot v = 0, \quad (2)$$

where v is the velocity vector and p is the pressure.

Figure 11:
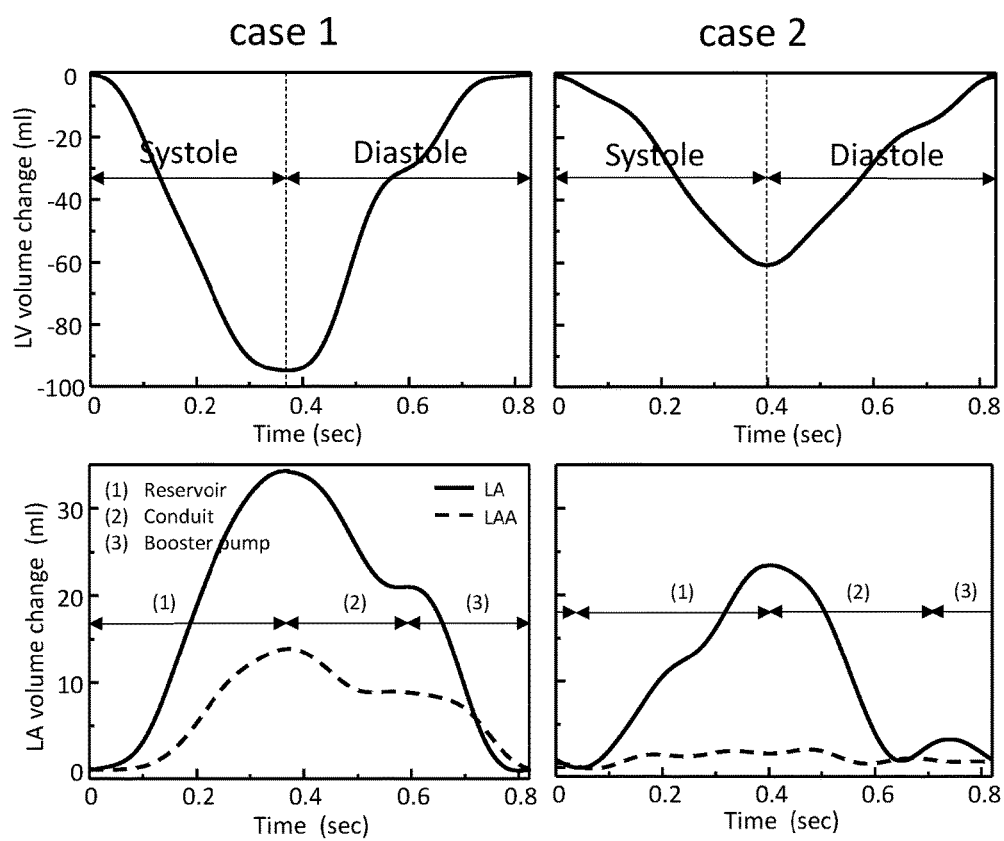
FIG. 11 shows graphs showing a time course of left ventricular volume change (a) and volume changes of left atrium (LA, solid line) and left atrial appendage (LAA, dashed line) (b) during the cardiac cycle. The left column (a-1, b-1) show case 1 and the right column (a-2, b-2) show case 2. Arrows in the top row (a) indicate the duration of systole and diastole; arrows in the bottom row (b) indicate the duration of each phase of LA function (reservoir, conduit and booster pump).

We treated the flow as laminar because the mean Reynolds number through the mitral valve (MV) during diastole was approximately 2,400 and 1,100 in case 1 and case 2, respectively. The blood flow across the MV was calculated from the changes in the LV volume during ventricular diastole measured from CT images. To minimize the computational cost and the impact of boundary conditions on the CFD analysis, we modeled the LV and each of the distal PV beyond the first bifurcation as a cylinder. We also interpolated the 4-D displacement fields smoothly in the PVs and the LV surfaces to avoid generating defect volume elements with high aspect ratio or non-orthogonality. We calculated the 4-D displacement field of the LV surface to allow the LV volume change measured from the CT images. We considered the MV to be closed during ventricular systole, open during ventricular diastole, and the time required for MV opening and closing to be negligible. We defined ventricular systole and diastole by the time course of the LV volume (FIG. 11, top row). We created two sets of volume mesh to calculate the blood flow depending on the MV configuration. When the MV was open, the volume mesh included the LA and the LV. When the MV was closed, the volume mesh included only the LA. The LA flow fields in transition between systole and diastole were interpolated using data mapping function in the OpenFOAM ("mapFields"). The initial velocity magnitude in the LV at the beginning of ventricular diastole was set to zero.

Computation.

The boundary conditions for the CFD studies were as follows. We determined the velocity vectors from time t to t+Δt in each time step at the surface boundary from the surface displacement fields in eq. 1. We employed the zero-gradient pressure condition at the distal end of each PV, where we determined the velocity by the flow direction: zero-gradient velocity for the PV inflow and a fixed velocity calculated from the flux through the boundary for the PV outflow. This boundary condition was chosen to reproduce both inflow and outflow of the PVs that are observed during the cardiac cycle in human heart[29]. The pressure p is determined such that the total pressure [p+½ρ(v·v)] is equal to zero. The MV annulus during ventricular systole was treated as a surface boundary. We conducted the blood flow analysis in each case with the time increment of 1×10$^{-4}$ sec. We defined convergence in each time step by the tolerance of velocity and pressure lower than 1×10$^{-5}$ and 1×10$^{-8}$, respectively. We computed a total of five cardiac cycles in each case.

Vortex Structures within the LA.

The 3-D vortex structure using $q_2$ criterion is often used to assess the cardiac flow characteristics[7,28,32]. It is calculated as the second invariant of the velocity gradient tensor $q_2$, given by $$q_2 = \tfrac{1}{2}(\Omega_{ij}\Omega_{ij} - S_{ij}S_{ij}) \quad (4)$$

where $\Omega_{ij}$ and $S_{ij}$ are the rotation and shear strain tensor, respectively. We used this criterion to visualize the vortex structures as the iso-surface of $q_2$ in the flow field.

Left Atrial Appendage Flow Characteristics.

We assessed the LAA flow characteristics by two indices. First, flow dissipation within the LAA was assessed by the flow kinetic energy in the LAA, defined by $$\text{Kinetic energy} = \int_{V_{LAA}} \tfrac{1}{2}\rho(v \cdot v)dV \quad (3)$$

where $V_{LAA}$ is the LAA volume. Second, blood stasis within the LAA was assessed by solving the transportation of the passive scalar $\phi$ in the flow field within the LAA. The passive-scalar transport analysis is one of the efficient and cost-effective techniques to visualize the blood flow characteristics[16,27] and to quantify blood flow stasis[12,22]. $\phi$ is expressed as the convection-diffusion equation, given by $$\frac{\partial \phi}{\partial t} + v \cdot (\nabla \phi) - D\nabla^2 \phi = 0 \quad (4)$$

where D is the diffusion coefficient of $1\times10^{-9}$ $m^2/sec$[16,28] (see Appendix S4, *Electronic Supplementary Material*).

At the beginning of the third cardiac cycle, $\phi$ was set to zero in the entire calculation domain except within the LAA where $\phi$ was set to one. To quantify blood stasis within the LAA, the residual fraction of $\phi$ was calculated as $$\text{Residual fraction} = \frac{1}{V_{LAA}^0}\int_{V_{LAA}} \phi dV \quad (5)$$

where $V_{LAA}^0$ is the LAA volume at the initial condition.

Results

Baseline Characteristics.

The baseline characteristics of each patient are shown in Table 5. The cycle length was 0.82 sec in both cases, equivalent to the heart rate of approximately 73 beats per minute. The LA volume in case 2 was approximately 2.3 times larger than that of case 1, whereas the LAA volume of case 2 was smaller than the case 1.

TABLE 5

Baseline characteristics.

|  |  | case 1 | case 2 |
|---|---|---|---|
| Cycle length | sec | 0.82 | 0.82 |
| LA volume (0% RR) | ml | 96.8 | 227.3 |
| LAA volume (0% RR) | ml | 13.9 | 8.47 |
| LV volume (0% RR) | ml | 135 | 160 |

LA, left atrium;
LV, left ventricle;
LAA, left atrial appendage;
RR, electrocardiographic R-R interval.

Time Course of Left Atrial and Left Atrial Appendage Volume.

The time course of LA and LAA volume with reference to the ventricular end-diastole was calculated in both cases from motion estimation results (FIG. 11, bottom row). The time course clearly showed three characteristic phases of LA function in both cases: 1) Reservoir phase: pulmonary venous return during the LV systole, 2) Conduit phase: pulmonary venous return during the LV early diastole, and 3) Booster pump phase: augmentation of the LV filling during the LV late diastole. In case 1, the LA volume rapidly increased and reached its peak (volume increase ~35 ml) at the end of the reservoir phase. The LA volume fell to a plateau at the end of the conduit phase, and further decreased to return the baseline at the end of the booster pump phase. The LAA volume showed a similar trend, reaching its peak (volume increase ~15 ml) at the end of the reservoir phase. Together, the LA and the LAA accounted for approximately 60% of the LV filling volume, which is consistent with our previous data in patients using cardiac MRI[14]. In case 2, the LA volume increased during the reservoir phase and reached its peak with a volume increase of ~20 ml. Unlike case 1, the LA volume then rapidly fell to close to the baseline during the conduit phase, and the booster pump phase had only a small volume increase (<5 ml). Furthermore, the reservoir and the conduit phases were longer, whereas the booster pump phase was shorter than those of case 1. The LAA volume change was consistently small during the entire cardiac phase (<5 ml).

Comparison Between CFD and Measurement Results.

The flow features at the LA-LAA junction (LAA os) was compared between the CFD results and clinical measurement using pulsed-Doppler TEE in case 1 [red arrow in FIG. 12A]. FIG. 12B shows the velocity magnitude measured over the cardiac cycle, which successfully captured four characteristic features of blood flow in this location[1]: 1) LAA filling: negative velocity with high magnitude; 2) Systolic reflection waves: variable numbers of alternating positive and negative velocities with diminishing magnitudes; 3) Early diastolic LAA flow: positive velocity with low magnitude; and 4) LAA contraction: positive velocity with high magnitude. In this specific patient, the early diastolic LAA flow included both positive and negative velocities [FIG. 12B], which likely represents a complex interaction between passive LAA emptying during rapid LV filling and continuous LAA filling from PV inflow (cite ref 1). To compare the CFD results against the TEE measurements, the corresponding sampling point and pulse direction were identified in the mesh [FIG. 12C]. FIG. 12D shows the velocity magnitude over time from the CFD results, which successfully captured the four characteristic features of blood flow with magnitudes similar to that of TEE measurements (arrows 1-4).

Left Atrial Global Flow Characteristics.

For the five cardiac cycles calculated in each case, flow characteristics reached a stable condition and became periodic within the first three cardiac phases. Therefore, we did not include the first two cardiac cycles but included only the last three cardiac cycles in the final analysis.

FIG. 13 shows the streamlines of blood flow in a representative cardiac cycle in the posterior view of the LA. In case 1, the blood flow from both the left PVs swirled clockwise along the top of the LA and the septum during the reservoir phase [FIG. 13 (case 1, 26% RR)]. During the conduit phase, this swirling flow was replaced by longitudinal flow of high velocity magnitude coming from all PVs to pass through the MV [FIG. 13 (case 1, 57% RR)]. At the end of the conduit phase, the longitudinal flow was replaced transiently by the swirling flow [FIG. 13 (case 1, 73% RR)]. During the booster pump phase the swirling flow immediately disappeared, followed by appearance of the flow coming into all PVs [FIG. 13 (case 1, 90% RR)]. Case 2 also generated the clockwise swirling flow in the posterior view [FIG. 13 (case 2, 20% RR)], which persisted throughout the cardiac cycle (FIG. 13 (case 2, 53% RR); FIG. 13 (case 2, 75% RR); and FIG. 13 (case 2, 90% RR)]. The velocity magnitudes were consistently small compared with those of case 1.

Figure 14:
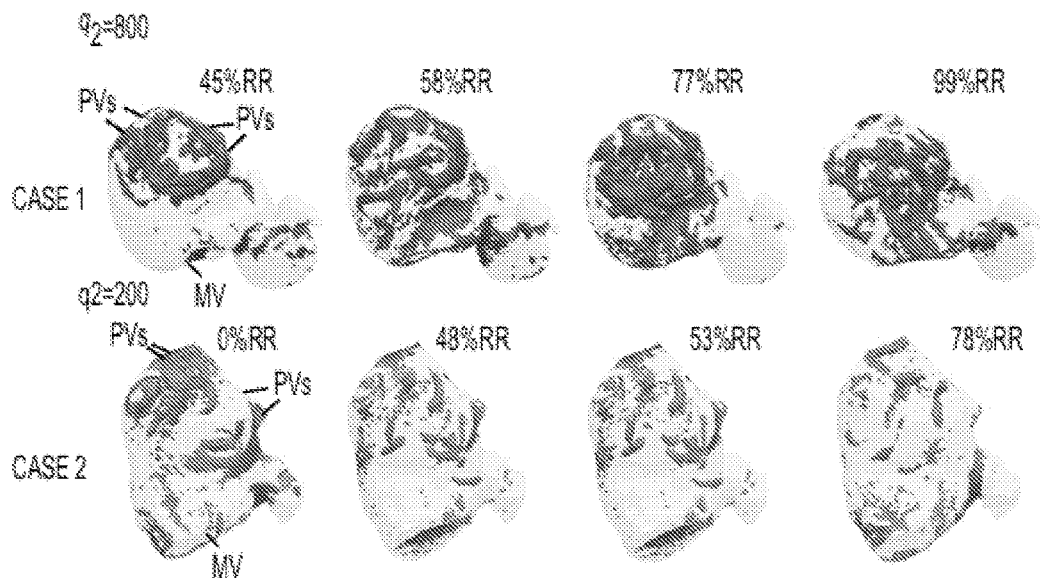
FIG. 14 shows models showing vortex structures during a representative cardiac cycle in the anterior view. Top row shows case 1 (q2=800); Bottom row shows case 2 (q2=200).

The 3-D vortex structures visualized by the iso-surface of $q_2$ are shown in FIG. 14. In case 1, the vortex rings were generated at the superior segment of the LA due to the flow coming out of each PV [FIG. 14 (case 1, 45% RR); FIG. 14 (case 1, 58% RR)]. The vortex rings became larger during the conduit phase [FIG. 14 (case 1, 77% RR)] and expanded in the whole LA [FIG. 14 (case 1; 99% RR)]. In contrast, in case 2 the vortex rings remained small consistently throughout the cardiac cycle.

Left Atrial Appendage Flow Characteristics.

Figure 15:
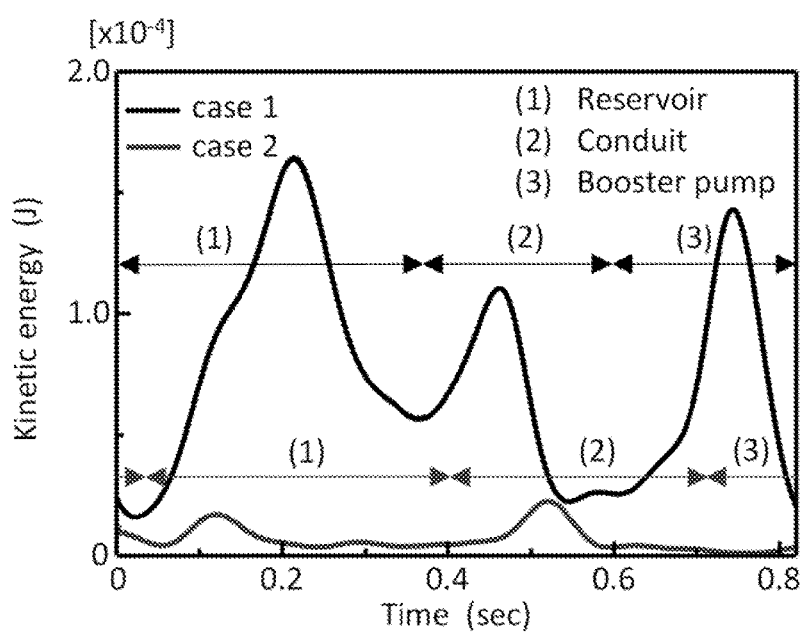
FIG. 15 is a graph showing a time course of left atrial appendage kinetic energy. The top line indicates case 1 and the bottom line indicates case 2. Arrows indicate each phase of LA function (reservoir, conduit and booster pump) in the respective cases.

FIG. 15 shows the time course of kinetic energy within the LAA in both cases. In case 1, kinetic energy was $0.3 \times 10^{-4}$ J at baseline, which reached the maximum at $1.7 \times 10^{-4}$ J during the mid-reservoir phase. It then decreased to $0.5 \times 10^{-4}$ J at the end of the reservoir phase but increased again to $1.1 \times 10^{-4}$ J until the mid-conduit phase. Kinetic energy then decreased again to $0.3 \times 10^{-4}$ J and remained low until the end of the conduit phase. It rapidly increased to $1.5 \times 10^{-4}$ J at the beginning of the booster pump phase and rapidly decreased to the baseline at $0.3 \times 10^{-4}$ J. In case 2, kinetic energy was approximately one order of magnitude smaller than that of case 1. As in case 1, kinetic energy slightly increased during the reservoir and the conduit phases. However, unlike case 1, there was no increase in kinetic energy during the booster pump phase. In addition, although the booster pump phase was shorter than that of case 1, kinetic energy did not go back to the baseline until ~50 ms into the next cardiac cycle due to a delay in each phase compared with case 1.

Figure 16A:
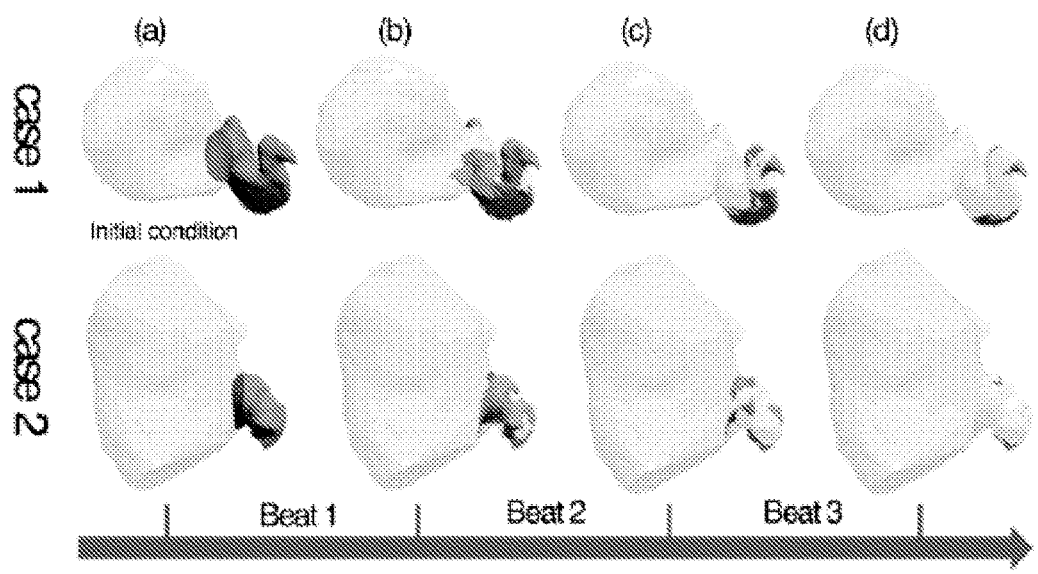
FIGS. 16A and 16B are a model and graph, respectively, showing left atrial appendage (LAA) blood emptying during the last three cardiac cycles (beat 1-3).
Figure 16B:
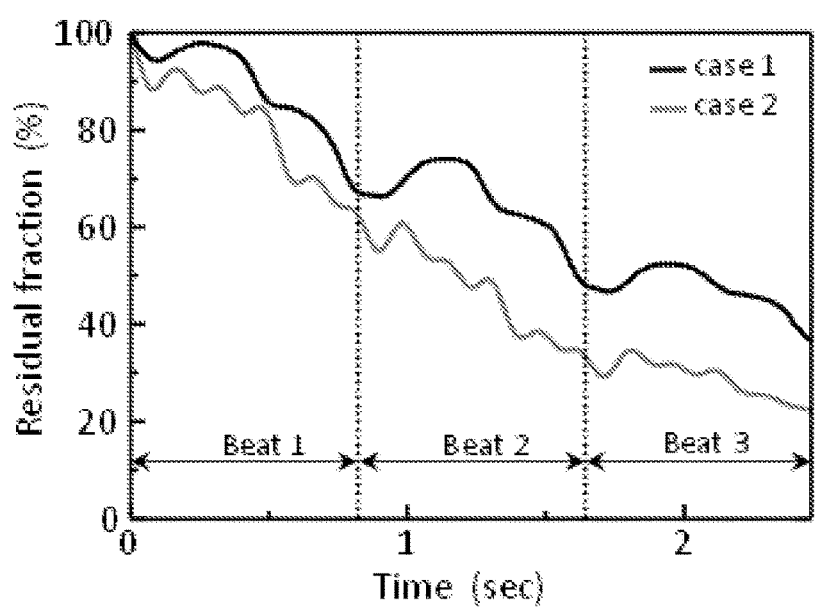

FIG. 16A shows the iso-surface of a passive scalar $\phi=0.8$ at ventricular end-diastole for the last three cardiac cycles (Beat 1-3). The results indicate that it took both cases three full cardiac cycles to empty the bulk of blood out of the LAA, although some amount of blood still remained at the periphery of the LAA at the end of Beat 3 (FIG. 16A (d)). The time course of residual fraction is shown in FIG. 16B. In FIG. 16B, the top line is case 1 and the bottom line is case 2. The residual fraction in both cases decreased with oscillation mainly due to systolic reflection waves with alternating positive and negative velocities during the reservoir phase. In both cases the residual fraction approached to zero at the end of beat 3, which is consistent with FIG. 16A.

Discussion

In this study, we performed a personalized LA blood flow analysis in two cases based on the patient-specific LA structure, endocardial surface motion and blood outflow into the LV. The time course of the LA volume clearly showed the three characteristic phases of the LA function in both cases (FIG. 11, bottom row), which is consistent with measurement results in our previous work using cardiac MRI[14]. However, the duration of each phase and the magnitude of volume change were substantially different between the two cases. These differences between the two cases are likely related to patient-specific LA structure and function. For example, the LA volume of case 2 was 2.3 times larger than that of case 1 (Table 5), and this abnormal structure may account for the longer reservoir and conduit phases and smaller magnitudes of volume changes in case 2 compared with those of case 1. These differences underscore the strength of our personalized approach, which provides clinically relevant patient-specific data.

The time course of the LA global blood flow in case 1 successfully recapitulates the blood flow characteristics of the healthy human LA[11], including 1) Reservoir phase: appearance of a swirling flow mainly from the left PVs in the LA; 2) Early conduit phase: disappearance of the swirling flow; 3) End of conduit phase: reappearance of the swirling flow; and 4) booster pump phase: disappearance of the swirling flow and appearance of the flow coming into all the PVs [FIG. 13 (top row)]. Our CFD framework also successfully reproduced the characteristic features of blood flow at the LAA os. Therefore, we believe that our computational framework for the personalized blood flow analysis is robust and can be used clinically to evaluate the global features of the LA blood flow field in individual patients.

It is important to note that the cardiac CT protocol from which motion estimation for the personalized blood flow analysis is performed is clinically practical. With a current state-of-the-art 320-slice multidetector CT scanner, the contrast-to-noise ratio sufficient for the motion estimation can be obtained with a radiation dose of <0.8 mSv using a low-dose cardiac functional CT protocol with retrospective ECG gating. This radiation dose is equivalent to that of less than two mammograms[2].

The LAA is the most common site of intracardiac thrombus[5], therefore evaluation of blood flow characteristics within the LAA is clinically important for assessment of cardioembolic stroke risk. We chose to use flow kinetic energy to quantify the strength of and evaluate the characteristics of blood flow within the LAA because it is a straightforward scalar parameter that is physically meaningful. We found that kinetic energy of the LAA was consistently high during the reservoir phase in case 1, whereas kinetic energy during the same phase in case 2 was substantially smaller (FIG. 15). These findings suggest that the high kinetic energy during the reservoir phase was caused by the LAA filling as the LA swirling flow entered the LAA [FIG. 13 (case 1, 26% RR)]. Since depressed LA reservoir function during normal sinus rhythm is associated with stroke[14], it is possible that the high kinetic energy during the reservoir phase contributes to maintaining the blood flow in and out of the LAA to minimize blood stasis that could lead to thrombogenesis. However, since neither case 1 nor case 2 had a history of stroke, further study with a larger sample size is needed to confirm this speculation.

In contrast to kinetic energy, the time course of LAA emptying by passive-scalar transport analysis was similar in both cases, despite the substantial difference in the LA structure and function. In case 1, the blood almost completely flowed away from the LAA by the end of Beat 3 but a small amount remained in the periphery of the LAA, primarily because of the complex LAA morphology. In case 2, the blood steadily flowed away from the LAA by the end of Beat 3, but remained in some small peripheral regions of the LAA similar to case 1 [FIG. 16A(d)]. In fact, it was unexpected to find a similar time course in these two cases with substantial difference in the degree of structural remodeling [FIG. 16B]. This somewhat counterintuitive finding implies that a smaller size and a relatively simple morphology of the LAA in case 2 may promote blood emptying and compensate for the flow dissipation due to structural remodeling. These findings are also consistent with previous reports that patients with a simpler LAA morphology are less associated with stroke than those with more complex LAA morphology[4,15,17]. Since our methodology allows personalized LA blood flow analysis that incorporates a number of clinically important patient-specific factors such as the LA/LAA size, LA/LAA function, and the LAA morphology, it can be used to improve our understanding of the mechanism of intracardiac thrombosis and stroke in individual patients with LA structural remodeling.

Conclusions.

We developed a computational framework to perform CT-based, personalized blood flow analysis in the LA. Our methodology successfully computes the LA blood flow using the patient-specific LA structure and function obtained from the cardiac CT images. Our personalized LA blood flow analysis is a clinically feasible methodology that can be used to improve our understanding of the mechanism of intracardiac thrombosis and stroke in individual patients with LA structural remodeling.

Mesh Convergence Study

Figure 17:
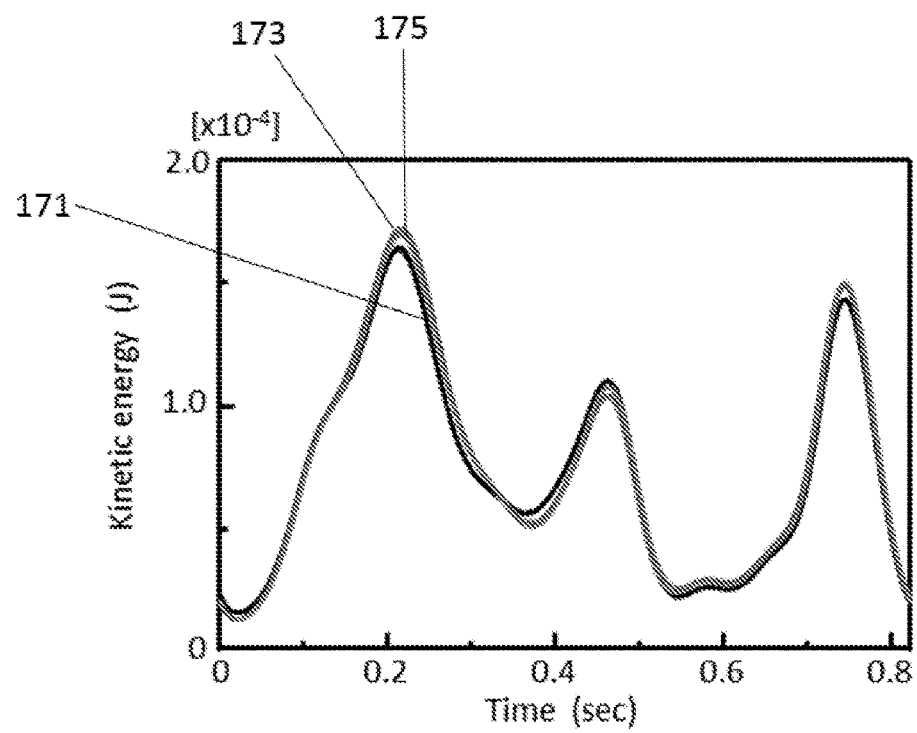
FIG. 17 is a graph showing a time course of left atrial appendage kinetic energy.
Figure 18:
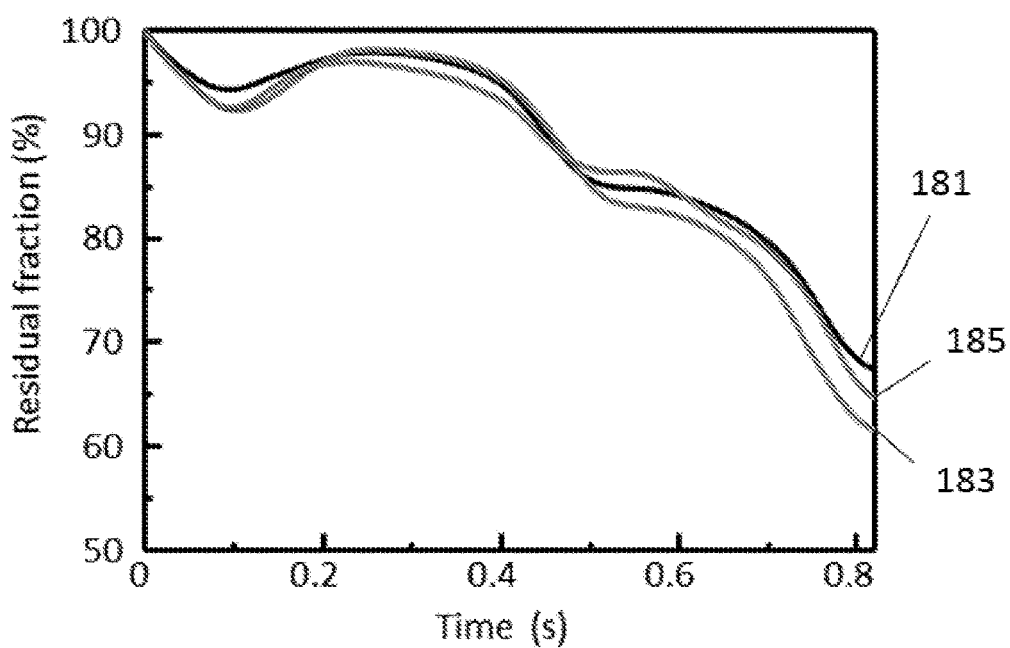
FIG. 18 is a graph showing a time course of residual fraction.
Figure 19:
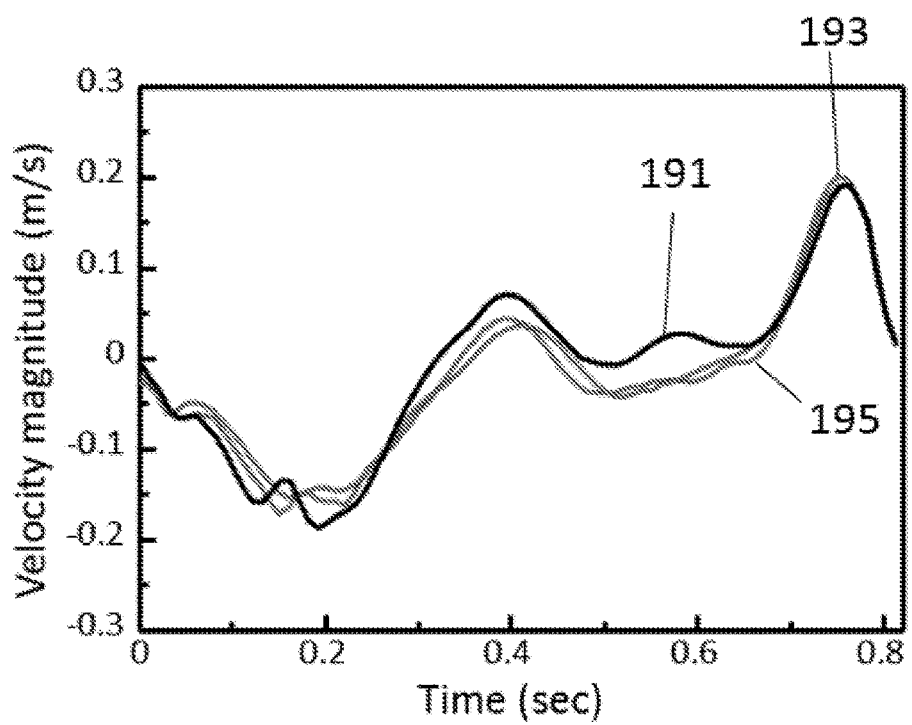
FIG. 19 is a graph showing Time course of flow velocity magnitude in the left atrial appendage (LAA).

To assess the impact of the size of volumetric elements on the CFD results, we created three different meshes with different base element sizes in case 1. The number of volumetric elements in the original mesh was 366,909; the coarse mesh included 260,443 (29% fewer than the original mesh); and the fine mesh included 601,081 (68% more than the original mesh). The results of the mesh converge study are shown below: left atrial appendage kinetic energy (FIG. 17; FIG. 15); residual fraction (FIG. 18; FIG. 16); and flow velocity magnitude (FIG. 19; FIG. 12). In FIG. 18, 181, 183 and 185 indicate the original, coarse and fine meshes, respectively.

For example, the time course of the kinetic energy (FIG. 17) from three different meshes agreed well with each other. In FIG. 17, 171, 173 and 175 indicate the original, coarse and fine meshes, respectively. The mean difference in the kinetic energy over a cardiac cycle was 6.6% between the original and the fine mesh and 6.4% between the original and the coarse mesh. The impact of volumetric element size on the time course of residual fraction (FIG. 18) and flow velocity magnitude in the left atrial appendage (FIG. 19) was similarly small. Of note, during the early diastolic LAA flow (arrow 3) in FIG. 19, the original mesh shows a positive velocity whereas the other two meshes show a negative velocity, both of which are of small magnitudes. In FIG. 19, 191, 193 and 195 indicate the original, coarse and fine meshes, respectively. This finding is indeed consistent with the clinical measurements from the transesophageal echocardiogram (TEE) shown in FIG. 12B in the main text, which included both positive and negative velocities of small magnitudes. This TEE finding likely represents a complex interaction between passive LAA emptying during rapid LV filling and continuous LAA filling from PV inflow.

Based on these results, we conclude that the size of volumetric elements does not substantially influence the solutions in this study.

CFD Solver in OpenFOAM

We solved the Navier-Stokes equation (eq. 2) and the continuity equation (eq. 3) with moving boundary conditions by the CFD scheme implemented in OpenFOAM ("pimpleDymFoam"). The time derivative is discretized by the first-order implicit Euler scheme and the convection term is treated by the total variation diminishing scheme using the Sweby limiter[30]. Volume mesh deformation is expressed by solving the Laplace equation. In this study, we assigned a zero-gradient boundary to the distal end of the pulmonary veins (PVs), and also to the mitral valve (MV) annulus during ventricular systole. We assigned u(t) calculated in eq. 1 to the remaining the nodes of the whole surface boundary.

Spatiotemporal Interpolation of the Displacement Field in the Pulmonary Veins and the Left Ventricle We interpolated the four-dimensional displacement fields smoothly in the pulmonary veins (PVs) and the left ventricular (LV) surfaces to avoid generating defect volume elements with high aspect ratio or non-orthogonality. We modeled the discrete displacement fields $\bar{u}_i$ given in 20 phases (i=1, 2, . . . , 20) assigned to all points of the surface meshes by the Laplace equation at each phase i.

$$\nabla^2 u_i = 0. \qquad (8)$$

We solved eq. 8 by a Galerkin finite element method using a linear shape function associated with nodes of the triangle surface mesh. For the LV surface, we assigned the Dirichlet boundary conditions to the displacement fields of the basal surface (=mitral valve annulus) derived from the motion estimation. We also constrained the displacement fields of the apical surface to zero except for the direction orthogonal to the basal surface, which allows displacement to represent the LV volume change measured from the CT images (FIG. 11, top row) at each phase. For the PV surface, we assigned the Dirichlet boundary condition to the displacement fields at each PV-left atrial (LA) junction derived from the motion estimation.

Convection-Diffusion Equation Solver in OpenFOAM

The solver for the convection-diffusion equation (eq. 6) for the passive-scalar transport analysis is implemented in OpenFOAM. The time derivative and the convection term are treated as in the CFD simulation. In our study, we assigned the following boundary conditions: endocardial surface, passive scalar=0; pulmonary veins (PVs), zero-gradient for flow coming into the PVs, and passive scalar=0 for flow going out of PVs.

REFERENCES FOR EXAMPLE 3

1. Agmon, Y., B. K. Khandheria, F. Gentile, and J. B. Seward. Echocardiographic assessment of the left atrial appendage. *J. Am. Coll. Cardiol.* 34:1867-1877, 1999.
2. Al-Issa, A., Y. Inoue, J. Cammin, Q. Tang, S. Nazarian, H. Calkins, E. K. Fishman, K. Taguchi, and H. Ashikaga. Regional function analysis of left atrial appendage using motion estimation CT and risk of stroke in patients with atrial fibrillation. *Eur. Hear. J.—Cardiovasc. Imaging jev207*, 2015.doi:10.1093/ehjci/jev207
3. Benjamin, E. J., R. B. D'Agostino, A. J. Belanger, P. A. Wolf, and D. Levy. Left Atrial Size and the Risk of Stroke and Death: The Framingham Heart Study. *Circulation* 92:835-841, 1995.
4. Di Biase, L., P. Santangeli, M. Anselmino, P. Mohanty, I. Salvetti, S. Gili, R. Horton, J. E. Sanchez, R. Bai, S. Mohanty, A. Pump, M. Cereceda Brantes, G. J. Gallinghouse, J. D. Burkhardt, F. Cesarani, M. Scaglione, A. Natale, and F. Gaita. Does the left atrial appendage morphology correlate with the risk of stroke in patients with atrial fibrillation? Results from a multicenter study. *J. Am. Coll. Cardiol.* 60:531-538, 2012.
5. Blackshear, J. L., and J. A. Odell. Appendage obliteration to reduce stroke in cardiac surgical patients with atrial fibrillation. *Ann. Thorac. Surg.* 61:755-759, 1996.
6. Brambatti, M., S. J. Connolly, M. R. Gold, C. a. Morillo, A. Capucci, C. Muto, C. P. Lau, I. C. Van Gelder, S. H. Hohnloser, M. Carlson, E. Fain, J. Nakamya, G. H. Mairesse, M. Halytska, W. Q. Deng, C. W. Israel, and J. S. Healey. Temporal relationship between subclinical atrial fibrillation and embolic events. *Circulation* 129:2094-2099, 2014.

7. Chnafa, C., S. Mendez, and F. Nicoud. Image-based large-eddy simulation in a realistic left heart. *Comput. Fluids* 94:173-187, 2014.
8. Daccarett, M., T. J. Badger, N. Akoum, N. S. Burgon, C. Mahnkopf, G. Vergara, E. Kholmovski, C. J. McGann, D. Parker, J. Brachmann, R. S. MacLeod, and N. F. Marrouche. Association of left atrial fibrosis detected by delayed-enhancement magnetic resonance imaging and the risk of stroke in patients with atrial fibrillation. *J. Am. Coll. Cardiol.* 57:831-838, 2011.
9. Daoud, E. G., T. V. Glotzer, D. G. Wyse, M. D. Ezekowitz, C. Hilker, J. Koehler, and P. D. Ziegler. Temporal relationship of atrial tachyarrhythmias, cerebrovascular events, and systemic emboli based on stored device data: A subgroup analysis of TRENDS. *Hear. Rhythm* 8:1416-1423, 2011.
10. Fatema, K., K. R. Bailey, G. W. Petty, I. Meissner, M. Osranek, A. A. Alsaileek, B. K. Khandheria, T. S. Tsang, and J. B. Seward. Increased left atrial volume index: potent biomarker for first-ever ischemic stroke. *Mayo Clin. Proc.* 83:1107-1115, 2008.
11. Fyrenius, A., L. Wigstrom, T. Ebbers, M. Karlsson, J. Engvall, and A. F. Bolger. Three dimensional flow in the human left atrium. *Heart* 86:448-455, 2001.
12. Goubergrits, L., U. Kertzscher, K. Affeld, C. Petz, D. Stalling, and H.-C. Hege. Numerical dye washout method as a tool for characterizing the heart valve flow: study of three standard mechanical heart valves. *ASAIO J.* 54:50-57, 2008.
13. Healey, J. S., S. J. Connolly, M. R. Gold, C. W. Israel, I. C. Van Gelder, A. Capucci, C. P. Lau, E. Fain, S. Yang, C. Bailleul, C. A. Morillo, M. Carlson, E. Themeles, E. S. Kaufman, and S. H. Hohnloser. Subclinical Atrial Fibrillation and the Risk of Stroke. *N. Engl. J. Med.* 366:120-129, 2012.
14. Inoue, Y. Y., A. Alissa, I. M. Khurram, K. Fukumoto, M. Habibi, B. A. Venkatesh, S. L. Zimmerman, S. Nazarian, R. D. Berger, H. Calkins, J. A. Lima, and H. Ashikaga. Quantitative Tissue-Tracking Cardiac Magnetic Resonance (CMR) of Left Atrial Deformation and the Risk of Stroke in Patients With Atrial Fibrillation. *J. Am. Heart Assoc.* 4:e001844-e001844, 2015.
15. Khurram, I. M., J. Dewire, M. Mager, F. Maqbool, S. L. Zimmerman, V. Zipunnikov, R. Beinart, J. E. Marine, D. D. Spragg, R. D. Berger, H. Ashikaga, S. Nazarian, and H. Calkins. Relationship between left atrial appendage morphology and stroke in patients with atrial fibrillation. *Heart Rhythm* 10:1843-9, 2013.
16. Kim, T., A. Y. Cheer, and H. A. Dwyer. A simulated dye method for flow visualization with a computational model for blood flow. *J. Biomech.* 37:1125-1136, 2004.
17. Kimura, T., S. Takatsuki, K. Inagawa, Y. Katsumata, T. Nishiyama, N. Nishiyama, K. Fukumoto, Y. Aizawa, Y. Tanimoto, K. Tanimoto, M. Jinzaki, and K. Fukuda. Anatomical characteristics of the left atrial appendage in cardiogenic stroke with low CHADS2 scores. *Hear. Rhythm* 10:921-925, 2013.
18. Kizer, J. R., J. N. Bella, V. Palmieri, J. E. Liu, L. G. Best, E. T. Lee, M. J. Roman, and R. B. Devereux. Left atrial diameter as an independent predictor of first clinical cardiovascular events in middle-aged and elderly adults: The Strong Heart Study (SHS). *Am. Heart J.* 151:412-418, 2006.
19. Koizumi, R., K. Funamoto, T. Hayase, Y. Kanke, M. Shibata, Y. Shiraishi, and T. Yambe. Numerical analysis of hemodynamic changes in the left atrium due to atrial fibrillation. *J. Biomech.* 48:472-478, 2015.
20. Ku, D. N. Blood Flow in Arteries. *Annu. Rev. Fluid Mech.* 29:399-434, 1997.
21. Miller, J. M., C. E. Rochitte, M. Dewey, A. Arbab-Zadeh, H. Niinuma, I. Gottlieb, N. Paul, M. E. Clouse, E. P. Shapiro, J. Hoe, A. C. Lardo, D. E. Bush, A. de Roos, C. Cox, J. Brinker, and J. A. C. Lima. Diagnostic performance of coronary angiography by 64-row CT. *N. Engl. J. Med.* 359:2324-2336, 2008.
22. Morales, H., I. Larrabide, A. Geers, L. San Roman, J. Blasco, J. Macho, and A. Frangi. A Virtual Coiling Technique for Image-Based Aneurysm Models by Dynamic Path Planning. *IEEE Trans. Med. Imaging* 1-11, 2012.doi:10.1109/TMI.2012.2219626
23. Ozer, N., L. Tokgozoglu, K. Oviinc, G. Kabakci, S. Aksoyek, K. Aytemir, and S. Kes. Left atrial appendage function in patients with cardioembolic stroke in sinus rhythm and atrial fibrillation. *J. Am. Soc. Echocardiogr.* 13:661-665, 2000.
24. Piccini, J. P., and J. P. Daubert. Atrial fibrillation and stroke: It's not necessarily all about the rhythm. *Hear. Rhythm* 8:1424-1425, 2011.
25. Pourmorteza, A., K. H. Schuleri, D. A. Herzka, A. C. Lardo, and E. R. McVeigh. A new method for cardiac computed tomography regional function assessment: Stretch quantifier for endocardial engraved zones (SQUEEZ). *Circ. Cardiovasc. Imaging* 5:243-250, 2012.
26. Russo, C., Z. Jin, R. Liu, S. Iwata, A. Tugcu, M. Yoshita, S. Homma, M. S. V Elkind, T. Rundek, C. Decarli, C. B. Wright, R. L. Sacco, and M. R. Di Tullio. LA volumes and reservoir function are associated with subclinical cerebrovascular disease: The CABL (Cardiovascular Abnormalities and Brain Lesions) study. *JACC Cardiovasc. Imaging* 6:313-324, 2013.
27. Seo, J. H., and R. Mittal. Effect of diastolic flow patterns on the function of the left ventricle. *Phys. Fluids* 25, 2013.
28. Seo, J. H., V. Vedula, T. Abraham, A. C. Lardo, F. Dawoud, H. Luo, and R. Mittal. Effect of the mitral valve on diastolic flow patterns. *Phys. Fluids* 26:121901, 2014.
29. Smiseth, O. A., C. R. Thompson, K. Lohavanichbutr, H. Ling, J. G. Abel, R. T. Miyagishima, S. V Lichtenstein, and J. Bowering. The pulmonary venous systolic flow pulse—its origin and relationship to left atrial pressure. *J. Am. Coll. Cardiol.* 34:802-809, 1999.
30. Sweby, P. K. High Resolution Schemes Using Flux Limiters for Hyperbolic Conservation Laws. *SIAM J. Numer. Anal.* 21:995-1011, 1984.
31. Tsang, T. S. M., W. P. Abhayaratna, M. E. Barnes, Y. Miyasaka, B. J. Gersh, K. R. Bailey, S. S. Cha, and J. B. Seward. Prediction of cardiovascular outcomes with left atrial size: Is volume superior to area or diameter? *J. Am. Coll. Cardiol.* 47:1018-1023, 2006.
32. Vedula, V., R. George, L. Younes, and R. Mittal. Hemodynamics in the left atrium and its effect on ventricular flow patterns. *J. Biomech. Eng.*, 2015.doi:10.1115/1.4031487
33. Wolf, P. A., R. D. Abbott, and W. B. Kannel. Atrial Fibrillation as an Independent Risk Factor for Stroke: The Framingham Study. *Stroke* 22:983-988, 1991.
34. Wong, J. M., C. C. Welles, F. Azarbal, M. A. Whooley, N. B. Schiller, and M. P. Turakhia. Relation of Left Atrial Dysfunction to Ischemic Stroke in Patients With Coronary Heart Disease (from the Heart and Soul Study). *Am. J. Cardiol.* 113:1679-84, 2014.
35. Zhang, L., and M. Gay. Characterizing left atrial appendage functions in sinus rhythm and atrial fibrillation using computational models. *J. Biomech.* 41:2515-23, 2008.

Example 4: Personalized Risk Prediction of Silent Brain Infarction Using Computational Fluid Dynamics Atrial fibrillation (Afib) is associated with an increased risk of stroke[1]. The current approach to estimate the risk of stroke in Afib patients is the $CHA_2DS_2\text{-}VAS_C$ scoring system [Cardiac failure, Hypertension, Age, Diabetes, Stroke/transient ischemic attack (TIA), VAscular disease, and Sex category], and oral anticoagulation (AC) is recommended for those with a score of 2 or greater[2]. Afib is also associated with silent brain infarction (SBI)[3-5], defined as evidence of brain infarction on imaging with no clinical symptoms. SBI accounts for cognitive decline associated with Afib, including cognitive impairment[6, 7] and dementia[8, 9], in stroke-free individuals. Although cognitive decline is a substantial burden on patients, families, and the health care system[10], the knowledge as to how to predict the risk of SBI in individuals with Afib is lacking. This is particularly important for individuals with the $CHA_2DS_2\text{-}VAS_C$ score of 0 or 1 who are considered a "low-risk" and thus not indicated for AC by the current guidelines.

Recently, extended electrocardiographic (ECG) monitoring revealed that most patients with acute stroke had no evidence of Afib within 1 month prior to the event[11, 12]. These findings strongly indicate that Afib may be a marker of elevated thromboembolic risk, but may not be mechanistically responsible for the events[13]. Instead, alterations in cardiac structure and function that serve as an arrhythmic substrate for Afib may be causally related to thromboembolism. For example, indices of left atrial (LA) structural remodeling, including larger LA size[14-19], larger extent of LA fibrosis[20], lower LA function[21], and lower LA appendage function[22] in sinus rhythm are known markers of stroke, SBI and cognitive decline[23-25].

Figure 20:
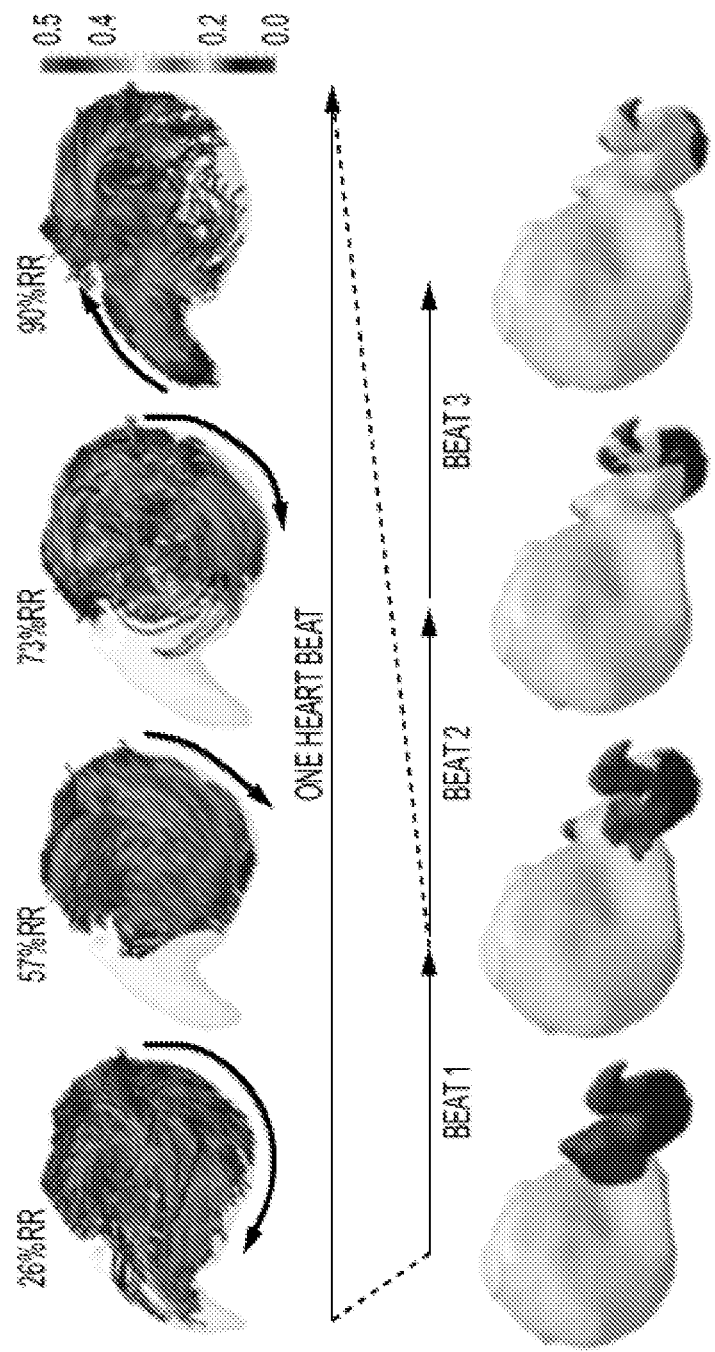
FIG. 20 is a schematic showing personalized Blood Flow Analysis in the Left Atrium. (Top) Streamlines of blood flow velocity over one heart beat (posterior view). (Bottom) Left atrial appendage blood emptying over three heart beats (anterior view).

We have developed a computational fluid dynamics (CFD) methodology[26] to conduct personalized blood flow analysis in the LA and LA appendage using the patient's cardiac CT (FIG. 20). CFD is a powerful tool to potentially link all the markers of structural remodeling and blood flow characteristics in the LA. This exciting new methodology can noninvasively quantify the blood flow not only in the left atrium but also in the LA appendage[27], the most common site of intracardiac thrombus[28, 29], which would otherwise require invasive transesophageal echocardiography (TEE). The CFD results agree well with clinical measurements by TEE.

We propose a time-sensitive study which aims to characterize LA structural remodeling in Afib patients using cardiac CT. Our objective is to investigate the impact of personalized LA blood flow analysis on cerebrovascular disease such as stroke, TIA and SBI. Our hypothesis is that personalized LA blood flow analysis in sinus rhythm can distinguish patients with and without a history of stroke and predict SBI independent of traditional stroke risk factors. This ancillary study represents a unique opportunity to leverage both our novel CT-based CFD framework and the strengths of Johns Hopkins University in quantitative and clinical cardiac electrophysiology to achieve the following two specific aims:

Aim 1. Determine how personalized LA blood flow analysis can distinguish patients with and without a history of stroke.

We will evaluate the cross-sectional association of personalized LA blood flow analysis with a history of stroke or TIA in a total of 30 patients, and adjust for traditional stroke risk factors such as the $CHA_2DS_2\text{-}VAS_C$ score. We will determine how the CFD parameters, such as flow velocity magnitude, vortex structures, LA appendage kinetic energy and LA appendage residual fraction, differ between patients with (n=15) and without a history of stroke or TIA (n=15).

Aim 2. Determine how personalized LA blood flow analysis can predict silent brain infarction.

We will evaluate the association of personalized LA blood flow analysis with SBI on brain MRI 6-12 months after cardiac CT in a pilot study of 30 patients, and adjust for traditional stroke risk factors and AC use.

REFERENCES FOR EXAMPLE 4

1. Wolf P A, Abbott R D, Kannel W B. Atrial fibrillation as an independent risk factor for stroke: The framingham study. *Stroke*. 1991; 22(8):983-988.
2. January C T, Wann L S, Alpert J S, Calkins H, Cigarroa J E, Cleveland J C, Jr., Conti J B, Ellinor P T, Ezekowitz M D, Field M E, Murray K T, Sacco R L, Stevenson W G, Tchou P J, Tracy C M, Yancy C W. 2014 aha/acc/hrs guideline for the management of patients with atrial fibrillation: A report of the american college of cardiology/american heart association task force on practice guidelines and the heart rhythm society. *Circulation*. 2014; 130(23):e199-267.
3. Kalantarian S, Ay H, Gollub R L, Lee H, Retzepi K, Mansour M, Ruskin J N. Association between atrial fibrillation and silent cerebral infarctions: A systematic review and meta-analysis. *Ann Intern Med*. 2014; 161(9): 650-658.
4. Ezekowitz M D, James K E, Nazarian S M, Davenport J, Broderick J P, Gupta S R, Thadani V, Meyer M L, Bridgers S L. Silent cerebral infarction in patients with nonrheumatic atrial fibrillation. The veterans affairs stroke prevention in nonrheumatic atrial fibrillation investigators. *Circulation*. 1995; 92(8):2178-2182.
5. Feinberg W M, Seeger J F, Carmody R F, Anderson D C, Hart R G, Pearce L A. Epidemiologic features of asymptomatic cerebral infarction in patients with nonvalvular atrial fibrillation. *Arch Intern Med*. 1990; 150(11):2340-2344.
6. Kalantarian S, Stern T A, Mansour M, Ruskin J N. Cognitive impairment associated with atrial fibrillation: A meta-analysis. *Ann Intern Med*. 2013; 158(5 Pt 1):338-346.
7. Thacker E L, McKnight B, Psaty B M, Longstreth W T, Jr., Sitlani C M, Dublin S, Arnold A M, Fitzpatrick A L, Gottesman R F, Heckbert S R. Atrial fibrillation and cognitive decline: A longitudinal cohort study. *Neurology*. 2013; 81(2):119-125. PubMed Central PMCID: PMC3770176.
8. Ott A, Breteler M M, de Bruyne M C, van Harskamp F, Grobbee D E, Hofman A. Atrial fibrillation and dementia in a population-based study. The rotterdam study. *Stroke*. 1997; 28(2):316-321.
9. Miyasaka Y, Barnes M E, Petersen R C, Cha S S, Bailey K R, Gersh B J, Casaclang-Verzosa G, Abhayaratna W P, Seward J B, Iwasaka T, Tsang T S. Risk of dementia in stroke-free patients diagnosed with atrial fibrillation: Data from a community-based cohort. *Eur Heart* 2007; 28(16): 1962-1967.
10. Alzheimer's A. 2015 alzheimer's disease facts and figures. *Alzheimers Dement*. 2015; 11(3):e332.
11. Daoud E G, Glotzer T V, Wyse D G, Ezekowitz M D, Hilker C, Koehler J, Ziegler P D, Investigators T. Temporal relationship of atrial tachyarrhythmias, cerebrovascular events, and systemic emboli based on stored device data: A subgroup analysis of trends. *Heart Rhythm.* 2011; 8(9):1416-1423.
12. Brambatti M, Connolly S J, Gold M R, Morillo C A, Capucci A, Muto C, Lau C P, Van Gelder I C, Hohnloser S H, Carlson M, Fain E, Nakamya J, Mairesse G H, Halytska M, Deng W Q, Israel C W, Healey J S, Investigators A. Temporal relationship between subclinical atrial fibrillation and embolic events. *Circulation.* 2014; 129(21):2094-2099.
13. Piccini J P, Daubert J P. Atrial fibrillation and stroke: It's not necessarily all about the rhythm. *Heart Rhythm.* 2011; 8(9):1424-1425.
14. Tsang T S, Barnes M E, Gersh B J, Takemoto Y, Rosales A G, Bailey K R, Seward J B. Prediction of risk for first age-related cardiovascular events in an elderly population: The incremental value of echocardiography. *J Am Coll Cardiol.* 2003; 42(7):1199-1205.
15. Benjamin E J, D'Agostino R B, Belanger A J, Wolf P A, Levy D. Left atrial size and the risk of stroke and death. The framingham heart study. *Circulation.* 1995; 92(4): 835-841.
16. Fatema K, Bailey K R, Petty G W, Meissner I, Osranek M, Alsaileek A A, Khandheria B K, Tsang T S, Seward J B. Increased left atrial volume index: Potent biomarker for first-ever ischemic stroke. *Mayo Clin Proc.* 2008; 83(10):1107-1115.
17. Di Tullio M R, Sacco R L, Sciacca R R, Homma S. Left atrial size and the risk of ischemic stroke in an ethnically mixed population. *Stroke.* 1999; 30(10):2019-2024.
18. Kizer J R, Bella J N, Palmieri V, Liu J E, Best L G, Lee E T, Roman M J, Devereux R B. Left atrial diameter as an independent predictor of first clinical cardiovascular events in middle-aged and elderly adults: The strong heart study (shs). *Am Heart J.* 2006; 151(2):412-418.
19. Tsang T S, Abhayaratna W P, Barnes M E, Miyasaka Y, Gersh B J, Bailey K R, Cha S S, Seward J B. Prediction of cardiovascular outcomes with left atrial size: Is volume superior to area or diameter? *J Am Coll Cardiol.* 2006; 47(5):1018-1023.
20. Daccarett M, Badger T J, Akoum N, Burgon N S, Mahnkopf C, Vergara G, Kholmovski E, McGann C J, Parker D, Brachmann J, Macleod R S, Marrouche N F. Association of left atrial fibrosis detected by delayed-enhancement magnetic resonance imaging and the risk of stroke in patients with atrial fibrillation. *J Am Coll Cardiol.* 2011; 57(7):831-838. PubMed Central PMCID: PMC3124509.
21. Inoue Y Y, Alissa A, Khurram I M, Fukumoto K, Habibi M, Venkatesh B A, Zimmerman S L, Nazarian S, Berger R D, Calkins H, Lima J A, Ashikaga H. Quantitative tissue-tracking cardiac magnetic resonance (cmr) of left atrial deformation and the risk of stroke in patients with atrial fibrillation. *J Am Heart Assoc.* 2015; 4(4):e001844.
22. Al-Issa A, Inoue Y, Cammin J, Tang Q, Nazarian S, Calkins H, Fishman E K, Taguchi K, Ashikaga H. Regional function analysis of left atrial appendage using motion estimation ct and risk of stroke in patients with atrial fibrillation. *Eur Heart J Cardiovasc Imaging.* 2015.
23. Karadag B, Ozyigit T, Ozben B, Kayaoglu S, Altuntas Y. Relationship between left atrial volume index and cognitive decline in elderly patients with sinus rhythm. *J Clin Neurosci.* 2013; 20(8):1074-1078.
24. Alosco M L, Gunstad J, Jerskey B A, Clark U S, Hassenstab J J, Xu X, Poppas A, Cohen R A, Sweet L H. Left atrial size is independently associated with cognitive function. *Int J Neurosci.* 2013; 123(8):544-552. PubMed Central PMCID: PMC4166650.
25. Oh J E, Shin J W, Sohn E H, Jung J O, Jeong S H, Song H J, Kim J M, Lee A Y. Effect of cardiac function on cognition and brain structural changes in dementia. *J Clin Neurol.* 2012; 8(2):123-129. PubMed Central PMCID: PMC3391617.
26. Otani T, Al-Issa A, Pourmorteza A, McVeigh E R, Wada S, Ashikaga H. A computational framework for personalized blood flow analysis in human left atrium. *Ann Biomed Eng.* In Press.
27. Alissa A, Inoue Y, Cammin J, Tang Q, Fishman E, Taguchi K, Ashikaga H. Regional dysfunction of left atrial appendage and its association with stroke in atrial fibrillation *Circulation.* 2014; 130:A18516.
28. Blackshear J L, Odell J A. Appendage obliteration to reduce stroke in cardiac surgical patients with atrial fibrillation. *Ann Thorac Surg.* 1996; 61(2):755-759.
29. Stoddard M F, Dawkins P R, Prince C R, Ammash N M. Left atrial appendage thrombus is not uncommon in patients with acute atrial fibrillation and a recent embolic event: A transesophageal echocardiographic study. *Journal of the American College of Cardiology.* 1995; 25(2): 452-459.

The embodiments illustrated and discussed in this specification are intended only to teach those skilled in the art how to make and use the invention. In describing embodiments of the invention, specific terminology is employed for the sake of clarity. However, the invention is not intended to be limited to the specific terminology so selected. The above-described embodiments of the invention may be modified or varied, without departing from the invention, as appreciated by those skilled in the art in light of the above teachings. It is therefore to be understood that, within the scope of the claims and their equivalents, the invention may be practiced otherwise than as specifically described.

We claim:
1. A method of performing a computerized cardiac simulation for at least one of diagnosis, risk assessment or treatment planning, comprising:
receiving, by a computer, a plurality of three-dimensional cardiac images of a subject's heart such that each one of the plurality of three-dimensional cardiac images corresponds to a different phase of a single cardiac cycle of said subject's heart;
modeling structure, using said computer, of a left atrium of said subject as a function of time using said plurality of three-dimensional cardiac images of said subject's heart;
modeling blood flow, using said computer, within, into and out of said left atrium of said subject as a function of time using computational fluidic dynamics and using structure of said left atrium obtained from at least one of said plurality of three-dimensional cardiac images or said modeling structure of said left atrium;
simulating at least one of time dependent structural function or time-dependent blood flow of said left atrium using results from said modeling structure and said modeling blood flow for a selected period of time; and
providing information to a user from said simulating of the at least one time dependent structural function or time-dependent blood flow of said left atrium for use in at least one of diagnosis, risk assessment or treatment planning for a physiological effect related to function of said left atrium of said subject.

2. The method of claim 1, wherein said plurality of three-dimensional cardiac images of said subject's heart are obtained from a noninvasive imaging modality.

3. The method of claim 1, wherein said plurality of three-dimensional cardiac images of said subject's heart are obtained from at least one of CT, MM, PET, SPECT, or ultrasound imaging.

4. The method of claim 1, wherein said plurality of three-dimensional cardiac images of said subject's heart are selected from a group consisting at least five three-dimensional cardiac images within a single cardiac cycle and at least twenty three-dimensional cardiac images within a single cardiac cycle.

5. The method of claim 1, wherein said providing information to said user from said simulating of the at least one time dependent structural function or time-dependent blood flow of said left atrium provides information for use in at least one of a diagnosis or risk assessment for stroke or dementia.

6. The method of claim 1, wherein said providing information to said user from said simulating provides information in a form of a three dimensional map.

7. The method of claim 6, wherein said three dimensional map is a dynamic map that changes in time in correspondence to said selected period of time of said simulating.

8. The method of claim 1, wherein said providing information to said user from said simulating provides information including at least one of a residual blood flow in the left atrium and/or a left atrial appendage, shear rate on a left atrial wall, vortex formation in the left atrium, blood flow across a mitral valve, changes in volume of a left ventricle, blood flow in a pulmonary vein, and blood flow across an aortic valve.

9. The method according to claim 1, wherein at least one of modeling structure or said modeling blood flow includes one selected from a group consisting of adding effects of one or more administered compound designed to change a fluid property of the blood, adding effects of at least one planned or actual treatment, and adding effects based on empirical data from said subject.

10. The method according to claim 1, wherein said plurality of three-dimensional cardiac images have a resolution of at least 2 mm.

11. A system for performing a computerized cardiac simulation for at least one of diagnosis, risk assessment or treatment planning, comprising:
a processor; and
a noninvasive imaging modality in communication with said processor,
wherein said processor is configured to receive a plurality of three-dimensional cardiac images of a subject's heart such that each one of the plurality of three-dimensional cardiac images corresponds to a different phase of a single cardiac cycle of said subject's heart,
wherein said processor is configured to generate a model structure of a left atrium of said subject as a function of time using said plurality of three-dimensional cardiac images of said subject's heart,
wherein said processor is configured to generate a model of blood flow within, into and out of said left atrium of said subject as a function of time using computational fluidic dynamics and using structure of said left atrium obtained from at least one of said plurality of three-dimensional cardiac images or said model structure of said left atrium,
wherein said processor is configured to generate a simulation of at least one of time dependent structural function or time-dependent blood flow of said left atrium using results from said model structure and said model of blood flow for a selected period of time, and
wherein said processor is configured to provide information to a user from said simulation of the at least one time dependent structural function or time-dependent blood flow of said left atrium for use in at least one of diagnosis, risk assessment or treatment planning for a physiological effect related to function of said left atrium of said subject.

12. The system of claim 11, further comprising a noninvasive imaging modality in communication with said processor.

13. The system of claim 11, further comprising an imaging system in communication with said processor, wherein said imaging system is configured to perform at least one of CT, MRI, PET, SPECT, or ultrasound imaging.

14. The system of claim 11, wherein said plurality of three-dimensional cardiac images of said subject's heart are selected from a group consisting at least five three-dimensional cardiac images within a single cardiac cycle and at least twenty three-dimensional cardiac images within a single cardiac cycle.

15. The system of claim 11, wherein said processor is further configured to provide information to said user from said simulation in a form of a three dimensional map.

16. The system of claim 15, wherein said three dimensional map is a dynamic map that changes in time in correspondence to said selected period of time of said simulation.

17. The system of claim 11, wherein said processor is further configured to provide information to said user including at least one of a residual blood flow in the left atrium and/or a left atrial appendage, shear rate on a left atrial wall, vortex formation in the left atrium, blood flow across a mitral valve, changes in volume of a left ventricle, blood flow in a pulmonary vein, and blood flow across an aortic valve from said simulating.

18. The system according to claim 11, wherein said processor is further configured to generate a model structure or a model of blood flow including one chosen from a group consisting of adding effects of one or more administered compound designed to change a fluid property of the blood, adding effects of at least one planned or actual treatment or generate a model of blood flow including adding effects of at least one planned or actual treatment, and adding effects based on empirical data from said subject or generate a model of blood flow including adding effects based on empirical data from said subject.

19. The system of claim 11, wherein said processor is further configured to receive a plurality of three-dimensional cardiac images having a resolution of at least 2 mm.

20. A computer readable medium comprising a non-transient computer readable program that upon execution by a processor causes the processor to perform a computerized cardiac simulation for at least one of diagnosis, risk assessment or treatment planning, comprising:
receiving, by a computer, a plurality of three-dimensional cardiac images of a subject's heart such that each one of the plurality of three-dimensional cardiac image corresponds to a different phase of a single cardiac cycle of said subject's heart;
modeling structure, using said computer, of a left atrium of said subject as a function of time using said plurality of three-dimensional cardiac images of said subject's heart;

modeling blood flow, using said computer, within, into and out of said left atrium of said subject as a function of time using computational fluidic dynamics and using structure of said left atrium obtained from at least one of said plurality of three-dimensional cardiac images or said modeling structure of said left atrium;

simulating at least one of time dependent structural function or time-dependent blood flow of said left atrium using results from said modeling structure and said modeling blood flow for a selected period of time; and providing information to a user from said simulating at least one of time dependent structural function or time-dependent blood flow of said left atrium for use in at least one of diagnosis, risk assessment or treatment planning for a physiological effect related to function of said left atrium of said subject.

* * * * *